United States Patent
Yokoyama et al.

(10) Patent No.: US 10,953,016 B2
(45) Date of Patent: Mar. 23, 2021

(54) SOLID DOSAGE FORM CONTAINING QUINAZOLINE DERIVATIVE

(71) Applicant: Shionogi & Co., Ltd., Osaka (JP)

(72) Inventors: Reiji Yokoyama, Hyogo (JP); Satoshi Sakuma, Hyogo (JP); Shohei Aikawa, Hyogo (JP); Hironori Tanaka, Osaka (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 16/481,552

(22) PCT Filed: Jan. 29, 2018

(86) PCT No.: PCT/JP2018/002626
§ 371 (c)(1),
(2) Date: Jul. 29, 2019

(87) PCT Pub. No.: WO2018/139626
PCT Pub. Date: Aug. 2, 2018

(65) Prior Publication Data
US 2019/0365773 A1 Dec. 5, 2019

(30) Foreign Application Priority Data
Jan. 30, 2017 (JP) .............................. JP2017-014310

(51) Int. Cl.
A61K 31/5377 (2006.01)
A61K 9/20 (2006.01)
A61K 9/28 (2006.01)

(52) U.S. Cl.
CPC ........ *A61K 31/5377* (2013.01); *A61K 9/2009* (2013.01); *A61K 9/2866* (2013.01)

(58) Field of Classification Search
None
See application file for complete search history.

(56) References Cited

U.S. PATENT DOCUMENTS 8,202,879 B2 * 6/2012 Kume .................. C07D 401/14
514/266.4
10,329,285 B2 6/2019 Tada et al.
10,513,513 B2 12/2019 Tada et al.

FOREIGN PATENT DOCUMENTS

EP 0 435 687 7/1991
EP 1 356 816 10/2003
EP 1 854 789 11/2007
(Continued)

OTHER PUBLICATIONS

International Preliminary Report on Patentability dated Aug. 8, 2019 in International Application No. PCT/JP2018/002626.
International Search Report (ISR) dated Apr. 10, 2018 in International (PCT) Application No. PCT/JP2018/002626.
Toshiyuki Yoneda et al., "The Antiproliferative Effects of Tyrosine Kinase Inhibitors Tyrphostins on a Human Squamous Cell Carcinoma in Vitro and in Nude Mice", Cancer Research, vol. 51, pp. 4430-4435, Aug. 15, 1991, cited in the specification.
(Continued)

*Primary Examiner* — Brian J Davis
(74) *Attorney, Agent, or Firm* — Wenderoth, Lind & Ponack, L.L.P.

(57) ABSTRACT

The present invention provides a formulation containing the compound represented by formula (I) or a pharmaceutically acceptable salt thereof, or their crystals, with a light-stabilizing substance and a polymer, particularly with one or more of titanium oxide and talc used as the light-stabilizing substance, and hypromellose used as the polymer, which hardly increase the amount of the related substances, and the formulation is hardly colored under light irradiation.

16 Claims, 1 Drawing Sheet

(56) References Cited

FOREIGN PATENT DOCUMENTS

| | | |
|---|---|---|
| EP | 1 944 029 | 7/2008 |
| EP | 2 374 801 | 10/2011 |
| EP | 3 150 573 | 4/2017 |
| EP | 3 330 267 | 6/2018 |
| JP | 3-200754 | 8/1991 |
| JP | 2013-14610 | 1/2013 |
| WO | 02/02552 | 1/2002 |
| WO | 02/060446 | 8/2002 |
| WO | 2006/090717 | 8/2006 |
| WO | 2007/052592 | 5/2007 |
| WO | 2009/079541 | 6/2009 |
| WO | 2009/079547 | 6/2009 |
| WO | 2010/074150 | 7/2010 |
| WO | 2015/182682 | 12/2015 |
| WO | 2017/018476 | 2/2017 |

OTHER PUBLICATIONS

Kaladhar B. Reddy et al., "Inhibition of Breast Cancer Cell Growth in Vitro by a Tyrosine Kinase Inhibitor", Cancer Research, vol. 52, pp. 3636-3641, Jul. 1, 1992, cited in the specification.

Valerie G. Brunton et al., "Cell-signaling targets for antitumour drug development", Cancer Chemother. Pharmacol., vol. 32, pp. 1-19, 1993, cited in the specification.

Yasuo Kokai et al., "Synergistic Interaction of p185c-neu and the EGF Receptor Leads to Transformation of Rodent Fibroblasts", Cell, vol. 58, pp. 287-292, Jul. 28, 1989, cited in the specification.

Bradley D. Anderson et al., C.G. Wermuth, (edited by C.G. Wermuth, The Practice of Medicinal Chemistry, last volume, in particular, p. 359 V—selection criteria of optimized salt), pp. 347-365, 1999, cited in ISR.

* cited by examiner

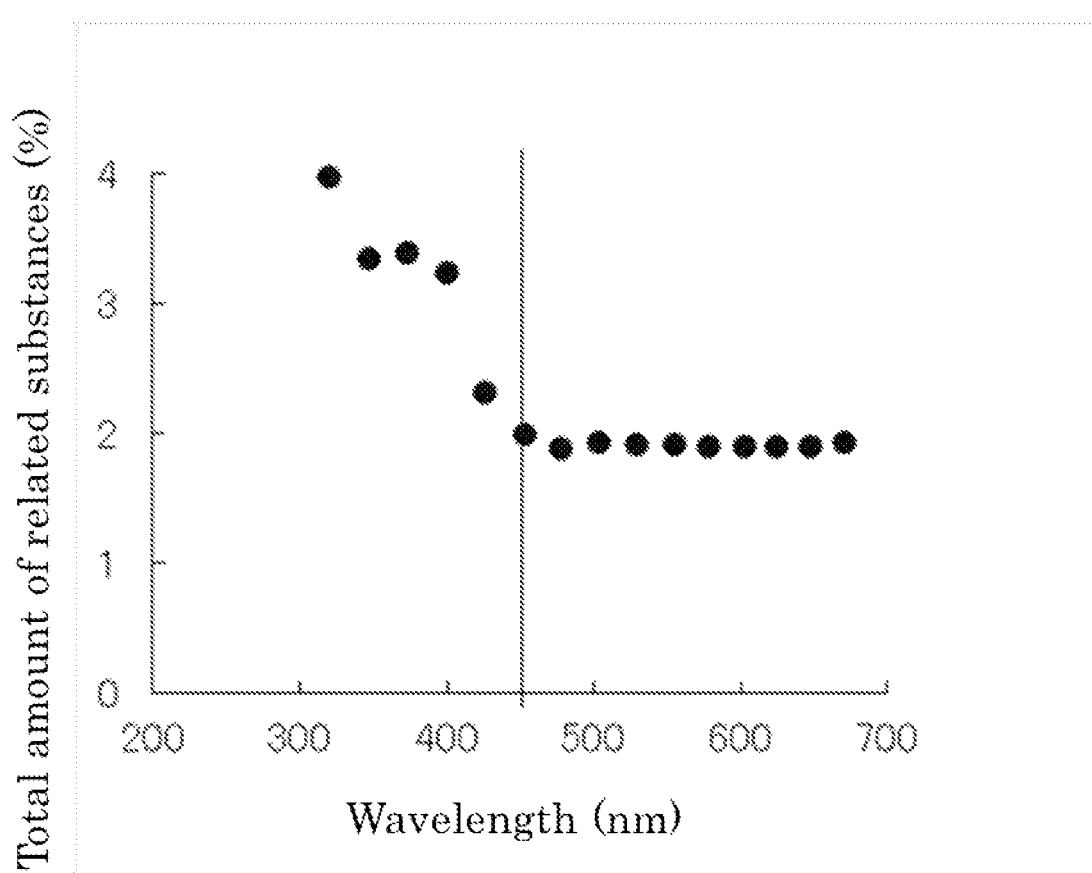

SOLID DOSAGE FORM CONTAINING QUINAZOLINE DERIVATIVE

TECHNICAL FIELD

The present invention relates to a solid dosage form containing quinazoline coated with a light-stabilizing substance and a polymer. The present formulation comprising the amount of the related substances hardly increases, and the formulation is hardly colored under light irradiation. More specifically, the present invention relates to a solid dosage form that is coated with a light-shielding substance or a light-absorbing substance against a wavelength shorter than 450 nm wavelength as a light-stabilizing substance, and a polymer.

BACKGROUND ART

Tyrosine kinase is an enzyme which phosphorylates tyrosine residues in substrate proteins, and is known to play an important role in an intracellular signal transduction system concerning cellular differentiation and proliferation. Especially, it is known that a growth factor receptor tyrosine kinase (hereinafter receptor tyrosine kinase) such as HER2 (also called as ErbB2 or Neu) and EGF receptor etc. are considerably involved in cancer development, and their activities increase in a variety of human cancers (Non-Patent Document 1, Non-Patent Document 2 and Non Patent Document 3).

Also, it is known that co-expression of EGF receptor and HER2 further promotes canceration by EGF receptor alone (Non-Patent Document 4) and a dual inhibitor that inhibits tyrosine kinase of both EGF receptor and HER2 is advantageous in having superior therapeutic effect in wider range of disease by synergistic effect of dual inhibition when compared with a EGF receptor or a HER2 selective inhibitor.

According to Patent Document 1, a quinazoline derivative represented by the following Formula:

[Formula 1]

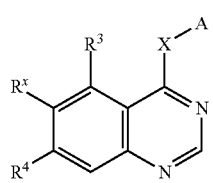

(II)

has dual inhibitory activity for EGF receptor and HER2, and is useful as a therapeutic and/or prophylactic agent for cancer. The following compound (VIII-102):

[Formula 2]

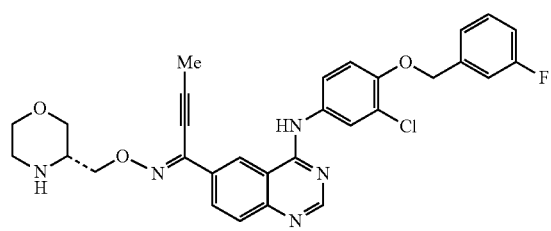

(VIII-102)

in a free base term is disclosed in an Example thereof, but neither an acid addition salt nor a solvate thereof is specifically disclosed. Also, crystals thereof are not specifically disclosed.

A method for producing a quinazoline derivative represented by Formula (VI'):

[Formula 3]

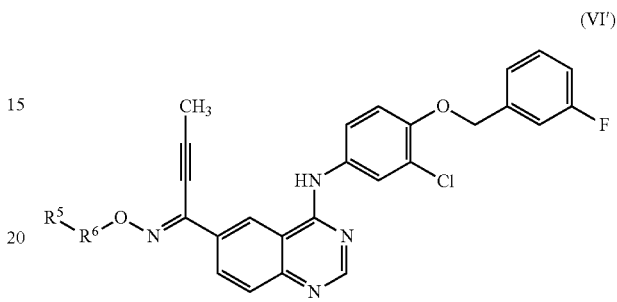

(VI')

is described in Patent Document 2. Also, the following compound (VI-15):

[Formula 4]

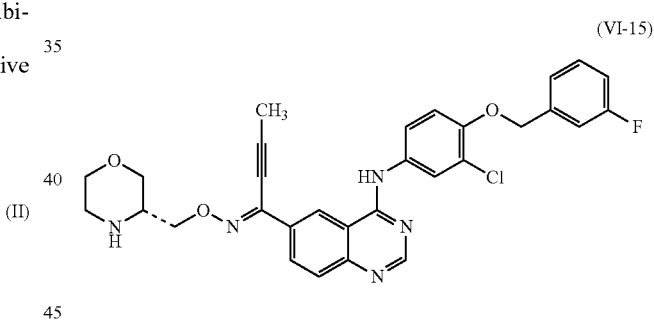

(VI-15)

in a free base form is disclosed in an Example thereof.

Patent Documents 3 and 4 disclose hydrate crystals and anhydride crystals of Lapatinib ditosylate that has a dual inhibitory activity for EGF receptor and HER2. Also, Patent Document 5 discloses anhydride crystals of a free base of Lapatinib.

Patent Documents 6 to 8 disclose pharmaceutical formulations having excellent light stability. However, Patent Documents 6 to 8 neither disclose nor suggest that the amount of the related substances in the solid dosage form containing the compound represented by formula (I) (compound (VIII-102) is described in Patent Document 1, compound (VI-15) is described in Patent Document 2), or its pharmaceutically acceptable salt increase, and the formulation is colored under light irradiation.

[Formula 5]

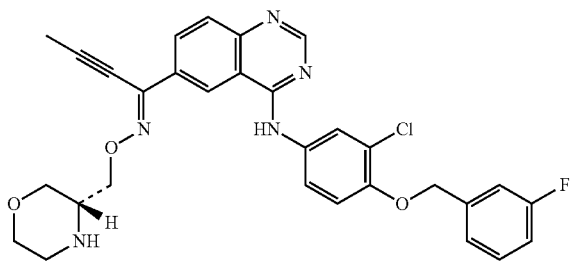

PRIOR ART REFERENCES

Patent Document

[Patent Document 1] International Publication No. WO 2000/090717
[Patent Document 2] International Publication No. WO 2010/07-1150
[Patent Document 3] International Publication No. WO 2002/002552
[Patent Document 4] International Publication No. WO 2009/079541
[Patent Document 5] International Publication No. WO 2009/079547
[Patent Document 6] Japanese Patent Laid-Open No. 2013-014610
[Patent Document 7] International Publication No. WO 2002/060446
[Patent Document 8] International Publication No. WO 2007/052592

Non-patent Document

[Non-patent Document 1] Cancer Research (Cancer Res.), 1991, vol. 51, p. 4430-4436
[Non-patent Document 2] Cancer Research (Cancer Res.). 1992, vol. 52, p. 3636-3641
[Non-patent Document 3] Cancer Chemotherapy and Pharmacology (Cancer Chemother. Pharmacol.), 1993, vol. 32, p. 1-19
[(Non-patent Document 4] Cell, 1939, vol. 58, p. 287-292

SUMMARY OF THE INVENTION

Problems to be Solved by the Invention

The inventors have found that the formulation containing the compound represented by formula (I) or its pharmaceutically acceptable salt, or their crystals in which the amount of the related substances increases, and the formulation is colored under light irradiation. An object of the present invention is to provide a formulation in which the amount of the related substances hardly increases, and which can be prevented coloring under light irradiation.

Means for Solving the Problem

As a result of having conducted diligent research, the inventors have found that the formulation containing the compound represented by formula (I) or its pharmaceutically acceptable salt, or their crystals by coating the surface of the formulation with a light-stabilizing substance and a polymer can be provided, in which the amount of the related substances hardly increases, and which is hardly colored under light irradiation, and thus the present invention was completed.

Also, the pharmaceutical ingredient may have substantially different physical properties according to the respective solid form. In the present invention, Inventors have found an acid addition salt or a solvate thereof of a compound represented by formula (I), or their crystals, more useful compared with the other solid forms, and then used them to produce the present formulation.

Namely, the present, invention relates to the following:
(1) A solid dosage form comprising a coating layer containing a light-stabilizing substance and a polymer, and a compound represented by formula (I):

[Formula 6]

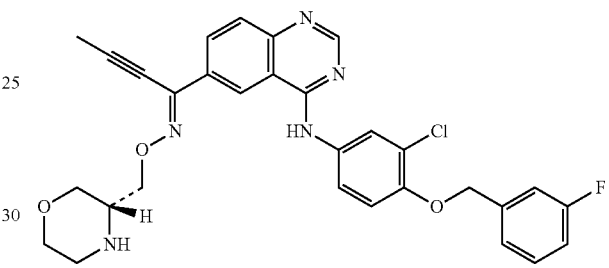

or its pharmaceutically acceptable salt as the active ingredient;
(2) the solid dosage form according to (1) above, wherein the light stabilizing substance in the coating layer is a substance that shields or absorbs light of wavelength shorter than 450 nm wavelength;
(3) the solid dosage form according to (1) above, wherein the light-stabilizing substance in the coating layer is one or more substance selected from the group consisting of edible tar dye, edible lake tar dye, edible natural dye, ferric oxide, titanium oxide and talc;
(4) the solid dosage form according to (1) above, wherein the light-stabilizing substance in the coating layer is one or more substance selected from the group consisting of Food Red No. 2, Food Red No. 3, Food Red No. 102, Food Red No. 104, Food Red No. 105, Food Red No. 106. Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, sodium copper chlorophyllin, copper chlorophyll, red oxide, red ferric oxide, yellow ferric oxide, black iron oxide, yellow oxide of iron, titanium oxide and talc;
(5) the solid dosage form according to (4) above, wherein the light-stabilizing substance in the coating layer is one or more substance selected from the group consisting of ferric oxide, yellow ferric oxide, black iron oxide, yellow oxide of iron, titanium oxide and talc;
(6) the solid dosage form according to (5) above, wherein the light-stabilizing substance in the coating layer is one or more substance selected from the group consisting of yellow ferric oxide, titanium oxide and talc;

(7) a solid dosage form comprising a coating layer containing one or more substance selected from the group consisting of Food Red No. 2, Food Red No. 3, Food Red No. 102. Food Red No. 104, Food Red No. 105, Food Red No. 106. Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, sodium copper chlorophyllin, copper chlorophyll, red oxide, red ferric oxide, yellow ferric oxide, black iron oxide, yellow oxide of iron, titanium oxide and talc, and a polymer, and a compound represented by formula (I):

[Formula 7]

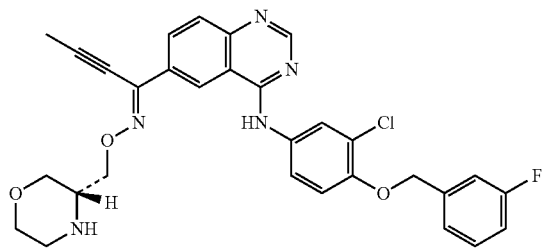

(I)

or its pharmaceutically acceptable salt as the active ingredient;

(8) the solid dosage form according to (7) above, comprising the coating layer containing yellow ferric oxide, titanium oxide and talc and the polymer, and the compound represented by formula (I) or its pharmaceutically acceptable salt as the active ingredient;

(9) the solid dosage form according to any one of (1) to (8) above, wherein the polymer in the coating layer is one or more substance selected from the group consisting of a cellulose-based polymer, an acrylic polymer and a vinyl polymer;

(10) the solid dosage form according to any one of (1) to (8) above, wherein the cellulose-based polymer in the coating layer is one or more substance selected from the group consisting of hypromellose, hydroxypropyl cellulose, carboxy methyl ethyl cellulose, hypromellose phthalate, hydroxypropyl methylcellulose acetate succinate and ethyl cellulose;

(11) the solid dosage form according to (10) above, wherein the cellulose-based polymer in the coating layer is hypromellose;

(12) the solid dosage form according to any one of (1) to (8) above, wherein the acrylic polymer in the coating layer is one or more substance selected from the group consisting of methacrylic acid copolymer, amino alkyl methacrylate copolymer E and amino alkyl methacrylate copolymer RS;

(13) the solid dosage form according to any one of (1) to (8) above, wherein the vinyl polymer in the coating layer is one or more substance selected from the group consisting of polyvinyl alcohol, polyvinylpyrrolidone and polyvinyl alcohol-methyl methacrylate-acrylate copolymer;

(14) the solid dosage form according to any one of (1) to (13) above, wherein the light-stabilizing substances in the coating layer are yellow ferric oxide, titanium oxide and the polymer in the coating layer is hypromellose;

(15) a solid dosage form comprising a coating layer containing yellow ferric oxide, titanium oxide, talc, and hypromellose, and a compound represented by formula (I):

[Formula 8]

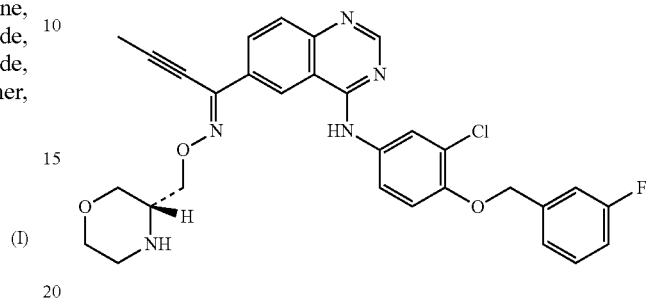

(I)

or its pharmaceutically acceptable salt;

(16) the solid dosage form according to any one of (1) to (15) above, wherein the amount of the light-stabilizing substance is 0.001 and 0.1 mg per 1 mm$^2$ of a specific surface area of the tablet;

(17) the solid dosage form according to any one of (1) to (16) above, wherein the increased amount of the related substances including the E-form of the compound represented by formula (I) is 0.3% or less, from the beginning of the experiment, when irradiated with light in a total irradiation amount of 1.2 million lux.hr;

(18) the solid dosage form according to any one of (1) to (17) above, wherein the color difference of the formulation is Δ20 or less when irradiated with light in a total irradiation amount of 1.2 million lux.hr;

(19) a solid dosage form comprising a compound represented by formula (I):

[Formula 9]

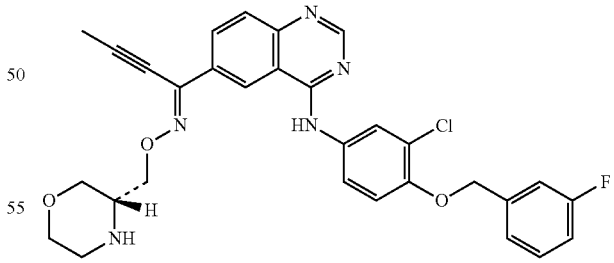

(I)

or its pharmaceutically acceptable salt as the active ingredient, wherein the increased amount of the related substances including the E-form of the compound represented by formula (I) is 0.3% or less from the beginning of the experiment, when irradiated with light in a total irradiation amount of 1.2 million lux.hr;

(20) a solid dosage form comprising a compound represented by formula (I):

[Formula 10]

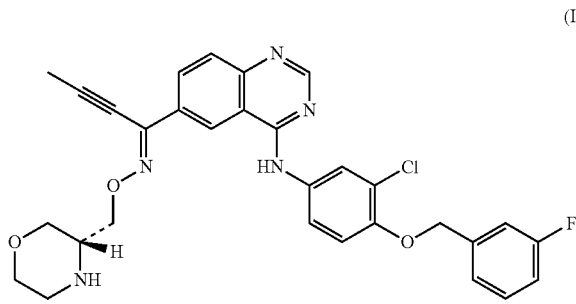 [SMILES: CC#C/C(=N\OC[C@H]1COCCN1)c1ccc2ncnc(Nc3ccc(OCc4cccc(F)c4)c(Cl)c3)c2c1]
(I)

or its pharmaceutically acceptable salt as the active ingredient, wherein the color difference of the formulation is Δ20 or less when irradiated with light in a total irradiation amount of 1.2 million lux.hr;

(21) the solid dosage form according to any one of (1) to (20) above, packaged with a light-shielding substance or a light-absorbing substance against a wavelength shorter than 450 nm wavelength:

(22) a solid dosage form comprising a compound represented by formula (I):

[Formula 11]

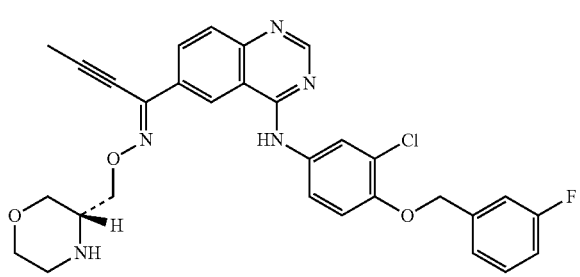
(I)

or its pharmaceutically acceptable salt as the active ingredient, packaged with a light-shielding substance or a light-absorbing substance against a wavelength shorter than 450 nm wavelength;

(23) the solid dosage form according to any one of (1) to (22) above, wherein the active ingredient is hydrochloride or p-toluenesulfonate of the compound represented by formula (I):

(24) the solid dosage form according to (23) above, wherein the active ingredient is monohydrochloride salt of the compound represented by formula (I);

(25) the solid dosage form according to any one of (1) to (24) above, which is a granule or a tablet;

(26) a method for analyzing a degradation product, wherein the amount of the related substances including the E-form of the compound represented by formula (I):

[Formula 12]

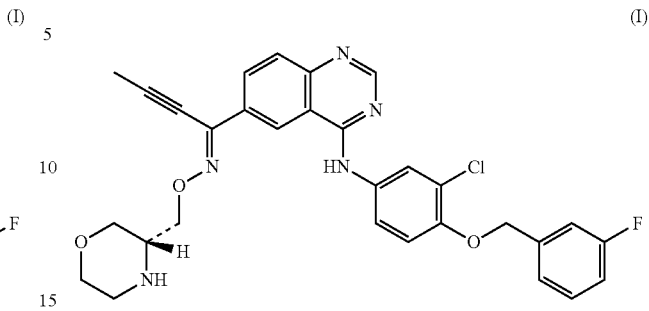
(I)

or its pharmaceutically acceptable salt as the active ingredient in a solid dosage form is measured by high-performance liquid chromatography;

(27) the E-form of the compound represented by formula (I):

[Formula 13]

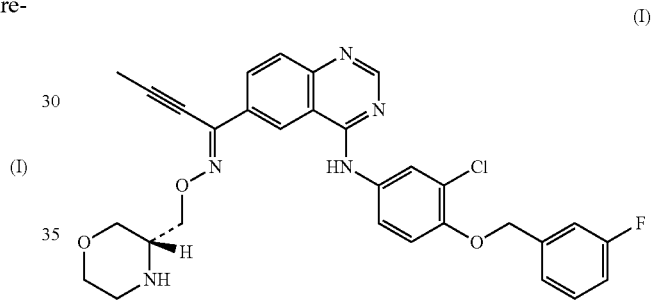
(I)

for use as a reference in conducting analysis;

(28) a method for reducing ΔE of the formulation as the color difference, wherein the amount of the E-form of the compound represented by formula (I):

[Formula 14]

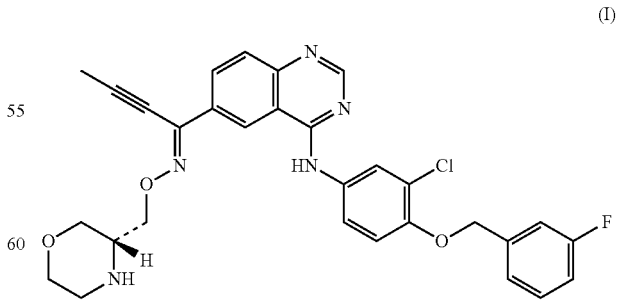
(I)

is reduced;

(29) a solid dosage form comprising hydrochloride of the compound represented by formula (I):

[Formula 15]

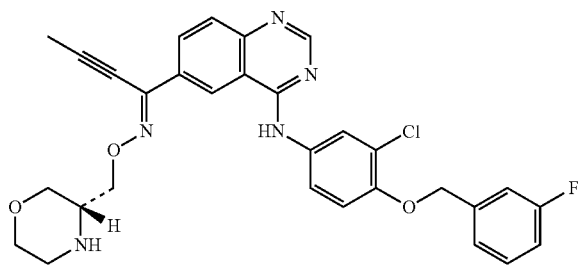

as the active ingredient;

(30) the solid dosage form according to (29) above, wherein the hydrochloride is monohydrochloride;

(31) the solid dosage form according to (29) or (30) above, wherein the monohydrochloride is one or more substance selected from the group consisting of Form I, Form V and Form VI.

Advantageous Effects of Invention

According to the present invention, even when a solid dosage form having a coating layer containing a light-stabilizing substance and a polymer, and the solid dosage form containing a compound represented by formula (I) or a pharmaceutically acceptable salt thereof is irradiated wilt light, the amount of related substance hardly increases from an initial stage of a test. In addition, the present formulation also hardly colores compared to the beginning of the study.

BRIEF DESCRIPTION OF DRAWINGS

The FIGURE illustrates change of the total amount of the related substances due to a change in the wavelength of light.

DESCRIPTION OF EMBODIMENTS

As an active ingredient in the formulation of the present invention, formula (I):

[Formula 16]

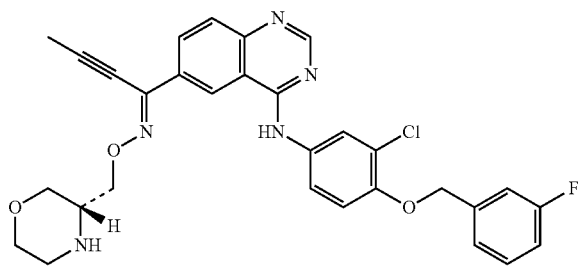

or its pharmaceutically acceptable salt are used. The formulation of the compound represented by formula (I) or its pharmaceutically acceptable salt is disclosed in patent references 1 or 2 and International Publication No. WO2015/182682.

Examples of pharmaceutically acceptable salts of the compound represented by formula (I) include salts of the compound represented by formula (I) and inorganic acids (such as hydrochloric acid, sulfuric acid, nitric acid, carbonic acid, hydrobromic acid, phosphoric acid, and hydroiodic acid) and organic acids (such as formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, and ethane-sulfonic acid). In particular, examples include salts of hydrochloric acid, p-toluenesulfunic acid, sulfuric acid, phosphoric acid, fumaric acid, tartaric acid, methanesulfonic acid and the like. The salts of hydrochloric acid and p-toluenesulfonic acid are particularly preferable. These salts can be formed by commonly performed methods.

For example, the compound represented by formula (I) is dissolved in various organic solvents and crystallized under acidic conditions, and thereby the acid addition salt of the compound represented by formula (I) or crystals thereof can be produced.

Hydrochloride or p-toluenesulfonate, or other pharmaceutically acceptable salts of the compound represented by formula (I), may form solvates (such as hydrates and ethanoates), co-crystals, and/or crystal polymorphs, and the present invention encompasses such various solvates, co-crystals, and crystal polymorphs as well. In the "solvate", arbitrary number of solvent molecules (such as water molecules) may be coordinated with hydrochloride, p-toluenesulfonate, or other pharmaceutically acceptable salts of the compound represented by formula (I). By being left to stand in the atmosphere, hydrochloride, p-toluenesulfonate, or other pharmaceutically acceptable salts of the compound represented by formula (I) may absorb water, resulting in attachment of adsorbed water or formation of hydrates. Also, recrystallization of hydrochloride, p-toluenesulfonate, or other pharmaceutically acceptable salts of the compound represented by formula (I) may form crystal polymorphs. The "co-crystal" means that hydrochloride, p-toluenesulfonate, or other pharmaceutically acceptable salts of the compound represented by formula (I) and counter molecules are present in the same crystal lattice, and may be formed with arbitrary number of counter molecules.

In monohydrochloride of the compound represented by formula (I), there are Form I, Form II, Form III, Form V, Form VI and Form VII, and ethanolate crystalline forms.

Also, there are crystalline forms of mono-p-toluenesulfonate; monosulfate and monosulfate hydrate; monophosphate and monophosphate hydrate; and monofumarate of the compound represented by formula (I).

Among the above crystalline forms, the crystalline forms of Form I, Form V and Form VI of monohydrochloride as well as crystalline form of mono-p-toluenesulfonate are more thermodynamically stable than other crystalline forms.

These crystal polymorphs can be produced in a differentiated manner according to the type of organic solvent used for crystallization and either of free base A (Example 1) of the compound represented by formula (I) or free base B (Example 2) of the compound represented by formula (I) is used as the compound represented by formula (I).

Monohydrochloride crystals Form I of the compound represented by formula (I) can be produced by dissolving free base A of the compound represented by formula (I) in methanol and causing crystallization in the presence of hydrochloric acid.

Monohydrochloride crystals Form II of the compound represented by formula (I) can be produced by dissolving free base A of the compound represented by formula (I) in a mixed solvent of methanol and ethyl acetate (methanol: ethyl acetate=1:1) and causing crystallization in the presence of hydrochloric acid.

Monohydrochloride crystals Form III of the compound represented by formula (I) can be produced by dissolving free base A of the compound represented by formula (I) in a mixed solvent of methanol and ethyl acetate (methanol: ethyl acetate=1:4) and causing crystallization in the presence of hydrochloric acid.

Monohydrochloride crystals Form V of the compound represented by formula (I) can be produced by dissolving free base B of the compound represented by formula (I) in 2-propanol and causing crystallization in the presence of acid.

Monohydrochloride crystals Form VI of the compound represented by formula (I) can be produced by dissolving free base A of the compound represented by formula (I) in 2-propanol and causing crystallization in the presence of hydrochloric acid.

Monohydrochloride crystals Form VII of the compound represented by formula (I) can be produced by dissolving crystalline form VI of monohydrochloride of the compound represented by formula (I) in 1,2-dimethoxyethane and causing crystallization.

Monohydrochloride ethanolate crystals of the compound represented by formula (I) can be produced by adding monohydrochloride crystalline form I as seed crystals to a mixed solution of ethyl acetate and ethanol.

Free base crystals of the compound represented by formula (I) can be produced by dissolving free base B of the compound represented by formula (I) in a mixed solution of hexane and ethyl acetate and causing crystallization.

Mono-p-toluenesulfonate crystalline form I of the compound represented by formula (I) can be produced by purifying free base A of the compound represented by formula (I) by an ordinary method, dissolving the free base in ethyl acetate, adding 1 mol/L of a solution of p-toluenesulfonic acid in methanol, and causing crystallization.

Monosulfate crystals of the compound represented by formula (I) can be produced by dissolving free base A of the compound represented by formula (I) in acetonitrile, adding 1 mol/L of sulfuric acid in methanol, and causing crystallization.

Monosulfate monohydrate crystals of the compound represented by formula (I) can be produced by dissolving trihydrate crystals of the compound represented by formula (I) in a mixed solution of acetonitrile and 2-propanol, adding 0.1 mol/L of sulfuric acid, then concentrating the mixture, further, adding a mixed solution of methanol and water, and shaking and then concentrating the mixture.

Monophosphate crystals of the compound represented by formula (I) can be produced by dissolving trihydrate crystals of the compound represented by formula (I) in a mixed solution of acetonitrile and 2-propanol, adding 0.1 mol/L of phosphoric acid, then concentrating the mixture, further, adding a mixed solution of ethanol and water, and shaking and then concentrating the mixture.

Monophosphate dihydrate crystalline form I of the compound represented by formula (I) can be produced by dissolving trihydrate crystals of the compound represented by formula (I) in a mixed solution of acetonitrile and 2-propanol, adding 0.1 mol/L of phosphoric acid, then concentrating the mixture, further, adding a mixed solution of methanol and water, and shaking and then concentrating the mixture.

Monofumarate crystalline form I of the compound represented by formula (I) can be produced by dissolving trihydrate crystals of the compound represented by formula (I) in a mixed solution of acetonitrile and 2-propanol, adding 0.1 mol/L of a mixed solution of fumaric acid in methanol and water, then concentrating the mixture, further, adding methanol and water, and shaking and then concentrating the mixture.

Monofumarate crystalline form II of the compound represented by formula (I) can be produced by dissolving trihydrate crystals of the compound represented by formula (I) in a mixed solution of acetonitrile and 2-propanol, adding 0.1 mol/L of a mixed solution of fumaric acid in methanol and water, then concentrating the mixture, further, adding acetonitrile and water, and shaking and then concentrating the mixture.

Hereinafter, methods for identifying the crystals of the present invention are described.

Unless otherwise noted, the numerical values provided in the description and the claims are approximate values. Numerical values vary due to the equipment calibration, equipment errors, purity of materials, crystal size, and sample size, and other factors.

As used herein, the "crystal" means a substance having an ordered arrangement of atoms, ions, molecules and the like that constitute a solid, and accordingly the substance has periodism and anisotropism. The degree of crystallinity of a crystalline form can be measured by various techniques including, for example, X-ray powder diffractometry, moisture sorption desorption, differential scanning calorimetry, thermogravimetry/differential thermal analysis, solution colorimetry, and dissolution properties.

X-Ray Powder Diffraction (XRPD)

In general, crystalline organic compounds consist of a large number of atoms that are arranged in a periodic array in three-dimensional space. The structural periodicity normally manifests physical properties, which can be explicitly distinguished by most spectroscopic probes (e.g., X-ray diffraction, an infrared spectrum, a Raman spectrum and solid state NMR). The X-ray powder diffraction (XRPD) is acknowledged to be one of the most sensitive analytical methods for measuring solid crystallinity. X-rays which are irradiated to crystals are reflected by the crystal lattice planes and mutually interfere. Then, only the diffraction lines in the direction which fulfill the conditions predicted by Bragg's law are intensified and the ordered diffraction lines corresponding to the periodicity of the structure are observed. On the other hand, in the case of amorphous solids, the well-ordered diffraction lines over a long-range are not observed. Amorphous solids usually show non-characteristic broad XRPD patterns because they do not have the ordered iteration periodicity in the structure, so that the diffraction phenomenon does not occur.

The crystalline forms of acid addition salts of the compound represented by formula (I) disclosed herein preferably have distinguishable X-ray powder diffraction profiles. For example, crystals containing monohydrochloride or mono-p-toluenesulfonate of the compound represented by formula (I) preferably are distinguishable from other crystalline forms according to the presence of characteristic diffraction peaks. The characteristic diffraction peaks as used herein are peaks selected from the observed diffraction patterns. The characteristic diffraction peaks are selected from preferably about 20, more preferably about 10, and most preferably about 5 peaks in a diffraction pattern.

In general, diffraction angles (2θ) in X-ray powder diffraction may have a margin of error within a range of ±0.2°, the value of a diffraction angle in X-ray powder diffraction should be understood as including values within a range of around ±0.2°. Therefore, the present invention includes not only crystals having totally the same diffraction angles of the peaks in X-ray powder diffraction, but also crystals having the same diffraction angles of the peaks within an error of around ±0.2°.

Hereinafter, the diffraction angles (2θ) of peaks were found in the observed powder X-ray diffraction spectrum in each crystal is described.

Diffraction angles (2θ) in X-ray powder diffraction spectrum of monohydrochloride crystalline form I of she compound represented by formula (I);
8.0°±0.2°, 14.1°±0.2°, 20.6°±0.2°, 21.0°±0.2°, 26.8°±0.2°.

Diffraction angles (2θ) in X-ray powder diffraction spectrum of monohydrochloride crystalline form II of the compound represented by formula (I);
11.3°±0.2°, 17.1°±0.2°, 25.6°±0.2°, 25.8°±0.2°, 26.4°±0.2°.

Diffraction angles (2θ) in X-ray powder diffraction spectrum of monohydrochloride crystalline form III of the compound represented by formula (I);
5.1°±0.2°, 9.9°±0.2°, 15.3°±0.2°, 21.4°±0.2°, 23.3°±0.2°.

Diffraction angles (2θ) in X-ray powder diffraction spectrum of monohydrochloride crystalline form V of the compound represented by formula (I);
23.9±0.2°, 25.9±0.2°, 26.2±0.2°, 26.7±0.2°, 28.4±0.2°.

Diffraction angles (2θ) in X-ray powder diffraction spectrum of monohydrochloride crystalline form VI of the compound represented by formula (I);
5.1°±0.2°, 16.3°±0.2°, 21.6°±0.2°, 23.2°±0.2°, 23.7°±0.2°.

Diffraction angles (2θ) in X-ray powder diffraction spectrum of monohydrochloride crystalline form VII of the compound represented by formula (I);
7.0°±0.2°, 12.3°±0.2°, 16.0°±0.2°, 19.1°±0.2°, 21.2°±0.2°.

Diffraction angles (2θ) in X-ray powder diffraction spectrum of monohydrochloride ethanolate crystals of the compound represented by formula (I);
8.3°±0.2°, 8.9°±0.2°, 12.9°±0.2°, 13.7°±0.2°, 4.7°±0.2°.

Diffraction angles (2θ) in X-ray powder diffraction spectrum of p-toluenesulfonate crystalline form I of the compound represented by formula (I);
13.7°±0.2°, 15.7°±0.2°, 20.0°±0.2°, 22.7°±0.2°, 25.3°±0.2°.

Diffraction angles (2θ) in X-ray powder diffraction spectrum of monosulfate crystals of the compound represented by formula (I);
0.2°±0.2°, 14.0°±0.2°, 14.5°±0.2°, 16.8°±0.2°, 22.9°±0.2°.

Diffraction angles (2θ) in X-ray powder diffraction spectrum of monosulfate monohydrate crystals of the compound represented by formula (I);
5.0°±0.2°, 9.9°±0.2°, 13.8°±0.2°, 14.7°±0.2°, 17.0°±0.2°.

Diffraction angles (2θ) in X-ray powder diffraction spectrum of monophosphate crystals of the compound represented by formula (I);
5.1°±0.2°, 6.2°±0.2°, 6.7°±0.2°, 9.8°±0.2°, 12.3°±0.2°.

Diffraction angles (2θ) in X-ray powder diffraction spectrum of monophosphate dihydrate crystalline form I of the compound represented by formula (I):
5.1°±0.2°, 6.5°±0.2°, 9.6°±0.2°, 12.9°±0.2°, 18.6°±0.2°.

Diffraction angles (2θ) in X-ray powder diffraction spectrum of monofumarate crystalline form I of the compound represented by formula (I);
8.0°±0.2°, 9.1°±0.2°, 16.1°±0.2°, 19.5°±0.2°, 19.9°±0.2°.

Diffraction angles (2θ) in X-ray powder diffraction spectrum of monofumarate crystalline form II of the compound represented by formula (I);
5.4°±0.2°, 9.1°±0.2°, 13.3°±0.2°, 13.7°±0.2°, 18.1°±0.2°.

The compound represented by formula (I) is an EGF receptor/HER2 dual inhibitor described in Patent Document 1, and a pharmaceutical composition containing the compound or its pharmaceutically acceptable salt as the active ingredient are used for preventing or treating cancer.

The present formulation can be used as "anticancer agent" and "therapeutic agent for cancer". For example, it can be used as for brain tumor (such as glioblastoma), urological cancer (such as bladder cancer and renal cancer), genital cancer (such as prostate cancer, ovarian cancer, and uterine cancer), lymphatic tumor, gastrointestinal cancer (such as stomach cancer, esophageal cancer, large intestine cancer, and colon cancer), throat cancer, lung cancer (such as lung adenocarcinoma, small cell lung cancer, non-small cell lung cancer), pancreatic cancer, breast cancer, head and neck career, and thyroid cancer. In particular, the anticancer agent and the therapeutic, agent for cancer are preferably used as therapeutic agents for breast cancer, brain tumor, bladder cancer, kidney cancer, prostate cancer, ovarian cancer, uterine cancer, lung cancer, pancreatic cancer, and head and neck cancer. More preferable is breast cancer.

The present formulation can be combined with another anticancer agent or the like. The present formulation can also be used in combination, or as a mixture, with another anticancer agent. Examples include trastuzumab, microtubule inhibitors [vinorelbine, taxane-based pharmaceutical agents (such as paclitaxel and docetaxel), irinotecan, eribulin mesylate], platinum based pharmaceutical agents (such as cisplatin, carboplatin, oxaliplatin, and nedaplatin), 5-FU-based pharmaceutical agents (such as capecitabine and 3-fluorouracil), breast cancer hormone therapies, HER2 inhibitors (trastuzumab, pertuzumab, lapatinib tosylate hydrate, neratinib, margetuximab), HER2 antibody conjugate drugs (trastuzumab emtansine (T-DM1), MM-302), HDAC inhibitors (entinostat), PARP inhibitors (talazoparib, niraparib, olaparib, veliparib), immunotherapeutic vaccines (such as nelipepimut-S), CDK4/6 inhibitors (ibrance, ribociclib, abemaciclib), PI3K/mTOR inhibitors (buparlisib, taselisib, everolimus, alpelisib), immune checkpoint inhibitors (such as PD1/PD-L1 inhibitors (nivolumab, atezolizumab, pembrolizumab), and the like. Also, two or more of the above anticancer agents can be used as combination.

A content of the compound represented by formula (I) or the pharmaceutically acceptable salt thereof in the present formulation is 1 to 80% by weight, preferably 5 to 75% by weight, and more preferably 10 to 70% by weight based on the total amount of the formulation.

The present formulation contains a light-stabilizing substance. Herein, the light-stabilizing substance may be any additive as long as it can stabilize against light, the compound represented by formula (I) or the pharmaceutically acceptable salt thereof, and can prevent color change of the formulation, and those described in The Japanese Pharmacopoeia, The Japanese Pharmaceutical Codex, The Japanese Pharmaceutical Excipients, and The Japan's Specifications and Standards for Food Additives can be used.

Examples of the light-stabilizing substance include a light-shielding substance having a light-shielding effect by shielding light, and a light-absorbing substance having an effect by absorbing light. In the present formulations, a light shielding substance having a light-shielding effect by shielding light of wavelength shorter than 450 nm wavelength or a light-absorbing substance having an effect by absorbing light of wavelength shorter than 150 nm wavelength are particularly preferred. Specific examples include a food tar dye, a food laked tar dye, a natural food dye, iron oxide, titanium oxide and talc. Preferable examples include Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 1 aluminum lake, Food Yellow No. 5 aluminum lake, Food Blue No. 1 aluminum lake, Food Blue No. 2 aluminum lake, carmine, copper chlorophyllin sodium, copper chlorophyll, colcothar, ferric oxide, yellow ferric oxide, black iron oxide, yellow iron oxide, titanium oxide and talc. Ferric oxide, yellow ferric oxide, black iron oxide, yellow oxide of iron, titanium oxide and talc are more preferred, and titanium oxide and talc of the light-shielding substances are particularly preferred.

The light-stabilizing substance of the present formulation may be blended in the formulation or may be coated on a surface of the formulation, and preferably, the light-stabilizing substance is coated on a surface of the formulation, namely, the light-stabilizing substance is contained in a coating layer. When the light-stabilizing substance is contained in the coating layer of the formulation, it absorbs or shields light from the outside of the formulation, and hence, the light stability of the compound represented by formula (I) contained in the formulation can be improved or the color change of the formulation can be prevented.

A content of the light-stabilizing substance in the present formulation may be any amount with which the compound represented by formula (I) or the pharmaceutically acceptable salt thereof is stabilized against light. Specifically, among the light stabilizing substances, a content of the light shielding substance such as titanium oxide or talc is 0.001 to 0.1 mg, preferably 0.00125 to 0.075 mg, and more preferably 0.0015 to 0.05 mg per $mm^2$ of a surface area of the formulation. Among light-stabilizing substance, the light-shielding substances such as titanium oxide and talc, are 0.00075-0.075 mg, preferably 0.001-0.05 mg, and more preferably 0.0015-0.03 mg per $mm^2$ of a surface area of the formulation; and the light-absorbing substances such as edible tar dyes, edible faked tar dyes, edible natural dyes, and iron oxide absorbing light are 0.0001-0.025 mg, preferably 0.0002-0.02 mg, and more preferably 0.0003-0.015 mg per $mm^2$ of a surface area of the formulation. Incidentally, the surface area of the formulation can be measured by CAD. In addition, the content of the light-stabilizing substance based on the weight of the uncoated tablet before forming the coating layer is specifically 0.01 to 4% by weight, preferably 0.05 to 3.5% by weight, more preferably 0.1 to 3% by weight. Among light-stabilizing substance, the light-shielding substances such as titanium oxide and talc, are 0.005-3% by weight, preferably 0.03-2.75% by weight, and more preferably 0.05-2.5% by weight, based on the weight of uncoated tablet before forming the coating layer; and the light-absorbing substances, such as edible tar dye, edible laked tar dye, edible natural dye, and iron oxide, absorb light in 0.001-1% by weight, preferably 0.0025-0.75% by weight, and more preferably 0.005*0.5% by weight, based on the weight of uncoated tablet before forming the coating layer. When the content is smaller, there is a possibility that the light stabilizing may be insufficient.

The present formulation contains a polymer. Herein, those described in The Japanese Pharmacopoeia, The Japanese Pharmaceutical Codex, The Japanese Pharmaceutical Excipients, and The Japan's Specifications and Standards for Food Additives can be used as the polymer. Specific examples include cellulose-based polymers such as hypromellose (hydroxypropyl methylcellulose), polyvinyl alcohol, ethyl cellulose, carboxymethyl ethyl cellulose, carmellose, carmellose sodium, hydroxyethyl cellulose, hydroxyethyl methyl cellulose, hydroxypropyl cellulose, hydroxypropyl methyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture; acrylic-based polymers such as an ethyl acrylate/methyl methacrylate copolymer dispersion, an aminoalkyl methacrylate copolymer, a methacrylic acid copolymer, a 2-methyl-5-vinylpyridine methyl acrylate/methacrylic acid copolymer, a dried methacrylic acid copolymer, and a dimethyl aminoethyl methacrylate/methyl methacrylate copolymer; vinyl-based polymers such as polyvinyl pyrrolidone, crospovidone, a carboxyvinyl polymer, polyvinyl acetal diethylamino acetate, polyvinyl alcohol, a polyvinyl alcohol/methyl methacrylate/acrylic acid polymer, and a polyvinyl alcohol copolymer; and carnauba wax, stearyl alcohol, shellac and cetanol, among which hypromellose (hydroxypropyl methylcellulose) is preferred.

The polymer of the present formulation may be blended in the formulation, or may be coated on the surface of the formulation, and preferably, the polymer is used as so-called a coating agent for coating the surface of the formulation to form the coating layer. When the polymer is contained in the coating layer of the formulation, it can coat, together with the light-stabilizing substance, the surface of the formulation, and hence, the light stability of the compound represented by formula (I) contained in the formulation can be improved, and the color change of the formulation can be prevented.

A content of the polymer in the coating layer herein may be any amount as long as the light-stabilizing substance can be coated on the surface of the formulation.

The present formulation may contain a disintegrating agent. Any disintegrating agents described in The Japanese Pharmacopoeia, The Japanese Pharmaceutical Codex, The Japanese Pharmaceutical Excipients, and The Japan's Specifications and Standards for Food Additives can be used as the disintegrating agent, and in using some kinds of disintegrating agents. Specific examples include croscarmellose sodium, crospovidone, carmellose calcium, carboxy methyl starch sodium, and low substituted hydroxypropyl cellulose, among which carmellose calcium is preferred.

A content of the disintegrating agent in the present formulation is 0.5 to 20% by weight, preferably 0.75 to 15% by weight, and more preferably 1 to 10% by weight based on the total amount of the formulation. When the content is smaller, there is a possibility that a solid dosage form, particularly in the form of a tablet, is not sufficiently disintegrated.

The present formulation may contain an excipient. Any excipients described in The Japanese Pharmacopoeia, The Japanese Pharmaceutical Codex, The Japanese Pharmaceutical Excipients, and The Japan's Specifications and Standards for Food Additives can be used as the excipient. Specific examples include sugar alcohols such as D-mannitol, xylitol, sorbitol, maltitol, lactitol and oligosaccharide alcohol, sugars such as xylose, glucose, fructose, maltose, lactose, sucrose, isomerized sugar, syrup, purified white sugar, white sugar, purified sucrose spherical granule, anhydrous lactose, and sucrose/starch spherical granule, semi-digested starch, glucose hydrate, powdered sugar, crystalline cellulose, microcrystalline cellulose, pullulan, β-cyclodextrin, aminoethyl sulfonic acid, candy powder, sodium chloride, citric acid, sodium citrate, glycine, calcium gluconate, L-glutamine, tartaric acid, potassium hydrogen tartrate, ammonium carbonate, dextran 40, dextrin, calcium lactate, povidone, macrogol (polyethylene glycol) 1500, macrogol 1540, macrogol 4000, macrogol (5000, anhydrous citric acid, DL-malic acid, sodium hydrogen phosphate, potassium dihydrogen phosphate, sodium dihydrogen phosphate, L-aspartic acid, alginic acid, carmellose sodium, hydrated silicon dioxide, crospovidone, calcium glycerophosphate, magnesium aluminosilicate, calcium silicate, magnesium silicate, light anhydrous silicic acid, synthetic aluminum silicate, flour, wheat starch, wheat germ flour, rice flour, rice starch, cellulose acetate phthalate, titanium oxide, magnesium oxide, dihydroxyaluminum aminoacetate, tribasic calcium phosphate, talc, calcium carbonate, magnesium carbonate, precipitated calcium carbonate, natural aluminum silicate, corn starch, granulated corn starch, potato starch, hydroxypropyl cellulose, hydroxypropyl starch, anhydrous calcium hydrogen phosphate, granulated anhydrous calcium hydrogen phosphate and calcium dihydrogen phosphate, among which sugar alcohols and crystalline cellulose are preferred, and D-mannitol, crystalline cellulose and microcrystalline cellulose are further preferred.

A content of the excipient in the present formulation is 10 to 90% by weight, preferably 15 to 81.5% by weight, and more preferably 20 to 85% by weight based on the total amount of the formulation.

When crystalline cellulose is used as an excipient in the present formulation, the content of crystalline cellulose is 5-35% by weight, preferably 7.5-32.5% by weight, more preferably 10-30% by weight, relative to the total amount of the formulations. When the content is smaller than this amount, there is a possibility that a granulation propaty in producing granules may be poor, or when the content is higher than this amount there is a possibility that dissolution property of the compound represented by formula (I) may not improve.

The present formulation may contain a binder. Any binders described in The Japanese Pharmacopoeia, The Japanese Pharmaceutical Codex, The Japanese Pharmaceutical Excipients, and The Japan's Specifications and Standards for Food Additives can be used as the binder. Specific examples include hydroxypropyl cellulose, corn starch, pregelatinized starch, partially pregelatinized starch, gum arabic, gum arabic powder, gelatin, agar, dextrin, pullulan, polyvinyl pyrrolidone, polyvinyl alcohol, crystalline cellulose, methyl cellulose, ethyl cellulose, carboxymethyl ethyl cellulose, carmellose, carmellose sodium, hydroxyethyl cellulose, hydroxyethyl methyl cellulose, hydroxypropyl cellulose and hypromellose, among which hydroxypropyl cellulose is preferred.

A content of the binder in the present formulation is 0.1 to 20% by weight, preferably 0.25 to 15% by weight, and more preferably 0.5 to 10% by weight based on the total amount of the formulation.

The present formulation may contain a lubricant. Any lubricants described in The Japanese Pharmacopoeia, The Japanese Pharmaceutical Codex, The Japanese Pharmaceutical Excipients, and The Japan's Specifications and Standards for Food Additives can be used as the lubricant. Specific examples include metal stearate, sucrose fatty acid ester, talc, hydrated silicon dioxide and sodium stearyl fumarate, among which metal stearate is preferred. Metal stearate includes magnesium stearate (Taihei Chemical Industry, Japan Oil, Sakai Chemical Industry), calcium stearate (Kanto Chemical, Japan Oil, Sakai Chemical Industry), among which magnesium stearate is preferred.

A content of the lubricant is usually 0.05 to 10% by weight, preferably 0.075 to 7.5% by weight, and more preferably 0.1 to 5% by weight based on the total amount of the formulation.

In order to efficiently perform a coating operation of the polymer, a plasticizer or an aggregation inhibitor may be contained in the coating agent for the coating layer of the present formulation, and those described in The Japanese Pharmacopoeia, The Japanese Pharmaceutical Codex, The Japanese Pharmaceutical Excipients, and The Japan's Specifications and Standards for Food Additives can be used. Specific examples include triethyl citrate, glycerin fatty acid ester, sucrose fatty acid ester, castor oil, talc and macrogol (polyethylene glycol), and the like.

The present formulation may contain a dye or a colorant, and any dyes described in The Japanese Pharmacopoeia, The Japanese Pharmaceutical Codex, The Japanese Pharmaceutical Excipients, and The Japan's Specifications and Standards for Food Additives can be used. The dye may be contained either in the tablet or in the coating layer. Specific examples of the dye include iron oxide, a tar dye and a natural dye. Examples of the iron oxide include ferric oxide, yellow iron oxide, yellow ferric oxide and black iron oxide. Examples of the tar dye include Food Yellow No. 1 aluminum lake, Food Blue No. 1 aluminum lake, Food Red No. 3 aluminum lake, Food Blue No. 1, Food Blue No. 2, Food Yellow No. 4, Food Yellow No. 5, Food Red No. 102, Food Red No. 2 and Food Red No. 3. Examples of the natural dye include a turmeric extract, β-carotene, a carotene solution, sodium copper chlorophyllin, copper chlorophyll, a naked barley green leaf extract powder, a dried powder of green juice of naked barley green leaves, a naked barley green leaf extract, titanium oxide and talc. Examples of the dye include those used as the light-stabilizing substance.

The present formulation may contain another additive if necessary in addition to those described above, and any additives described in The Japanese Pharmacopoeia, The Japanese Pharmaceutical Codex, The Japanese Pharmaceutical Excipients, and The Japan's Specifications and Standards for Food Additives can be used. Besides, a content of such additives may be an arbitrary rate. Specific examples of the additive used in addition to those described above include a perfume, a fluidizing agent and a flavoring agent.

Specific examples of the perfume include an orange extract, orange oil, caramel, camphor, cinnamon oil, spearmint oil, a strawberry extract, a chocolate extract, cherry flavor, spruce oil, pine oil, peppermint oil, vanilla flavor, a bitter extract, fruit flavor, a peppermint extract, mixture flavor, mint flavor, menthol, a lemon powder, lemon oil and rose oil.

Specific examples of the fluidizing agent include hydrated silicon dioxide, light anhydrous silicic acid, crystalline cellulose, synthetic aluminum silicate and talc. Specific examples of the flavoring agent include aspartame, sucralose, glycine, sodium chloride, magnesium chloride, hydrochloric acid, dilute hydrochloric acid, citric acid and a salt thereof, anhydrous citric acid, L-glutamic acid and a salt thereof, succinic acid and a salt thereof, acetic acid, tartaric acid and a salt thereof, sodium hydrogen carbonate, fumaric acid and a salt thereof, malic acid and a salt thereof, glacial acetic acid, disodium inosinate and honey.

The present formulation may be a solid dosage form. Specifically, it may be a granule, a fine granule, a tablet, a powder, a capsule, a pill or the like, and a granule and a tablet are preferable.

A method for manufacturing a granule of the present formulation is not especially limited, and specifically is a method in which the active ingredients and additives such as a disintegrant and an excipient are mixed to produce a mixed powder, and the mixed powder is granulated, and is preferably a wet granulation method in which granulation is performed with water, water containing a binder, a solvent added, a dry granulation method in which compression molding is performed without using water, or a melt granulation method. As a machine to be used for mixing the active ingredients, additives and the like, a V-shaped mixer, a container blender can be used. Besides, as a machine to be used for granulation, a wet pellet mill, a fluidized bed granulator, a stirring granulator, a dry crushing granulator, a melt extrusion granulator can be used.

A method for producing a tablet, of the present formulation is not especially limited, and specifically is a tableting method in which a granule is produced by the above-described method, a disintegrating agent and a lubricant are mixed with the granule, and thus obtained mixed granule is tableted with a tableting machine. As a machine to be used for mixing the active ingredients, additives and the like, a V-shaped mixer or a container blender can be used. Besides, as the tableting machine, a single punch tableting machine, a rotary tableting machine or the like can be used.

After producing the granule or the tablet of the present formulation as described above, the resultant granule or the tablet, may be coated with the light-stabilizing substance and the polymer to form the coating layer thereon in some cases. When the coating layer is formed on the granule, a fluidized bed granulation coating machine, a fluidized bed rolling coating machine or the like can be used. When the coating layer is formed on the tablet, a pan coating machine, a vented coating machine or the like can be used. In forming the coating layer using the light-stabilizing substance and the polymer on the surface of the formulation, the light-stabilizing substance and the polymer are dissolved or suspended in water or a solvent, such as ethanol to prepare a coating solution. With the granule or the tablet caused to flow in the coating machine, the coating solution is sprayed onto the granule or the tablet, and the resultant is dried to form the coating layer.

When the present formulation is irradiated with light, the amount of a related substance hardly increases from the start of an experiment, and a color difference of the formulation hardly changes. Specifically, when the formulation is put in an exposure apparatus and is irradiated with light in a total irradiation amount of 1.2 million lux.hr, the color difference of the formulation is 420 or less, and the increased amount of the related substances including the E-form of the optical isomer of the compound represented by formula (I) is 0.3% or less, from the beginning of the experiment.

In addition, the amount of related substances, including the E-form of the compound represented by formula (I), can be measured by high-performance liquid chromatography. At this point, the E-form of the compound represented by formula (I) can be used as a reference in measuring the related substance. Furthermore, when the amount of the E-form of the compound represented by formula (I) is reduced, there is a possibility that the color difference ΔE of the formulation can be decreased.

Incidentally, the E-form of the compound represented by formula (I):

[Formula 17]

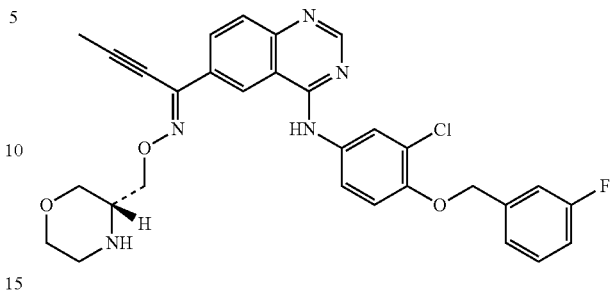

(I)

is described below

[Formula 18]

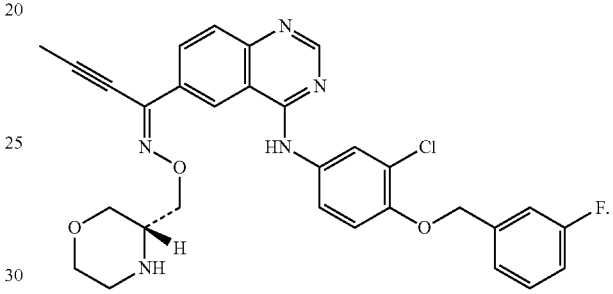

A content of the compound represented by formula (I) in a tablet may be any content as long as a patient can easily take the tablet and the tablet can be produced, and is 10 to 400 mg, preferably 12.5 to 350 mg, and more preferably 15 to 300 mg per tablet.

The present invention is a solid dosage form having a coating layer containing a light-stabilizing substance and a polymer, and containing a compound represented by formula (I) or a pharmaceutically acceptable salt thereof as the active ingredient.

Preferably, it is a solid dosage form using, as the light-stabilizing substance contained in the coating layer, a substance that shields or absorbs light of wavelength shorter than 450 nm wavelength.

The light-stabilizing substance is preferably one or more substance selected from the group consisting of a food tar dye, a food laked tar dye, a natural food dye, iron oxide, titanium oxide and talc.

The light-stabilizing substance is preferably one or more substance selected from the group consisting of Food Red No. 2, Food Red No. 3, Food Red No. 102, Food Red No. 104, Food Red No. 105, Food Red No. 106, Food Yellow No. 4, Food Yellow No. 5, Food Green No. 3, Food Blue No. 1, Food Blue No. 2, Food Red No. 3 aluminum lake, Food Yellow No. 4 aluminum lake, Food Yellow No. 5 aluminum lake, Food Blue No. 1 aluminum lake, Food Blue No. 2 aluminum lake, carmine, copper chlorophyllin sodium, copper chlorophyll, colcothar, ferric oxide, yellow ferric oxide, black iron oxide, yellow iron oxide, titanium oxide or talc.

In particular, one or more substance selected from the group consisting of ferric oxide, yellow ferric oxide, black iron oxide, yellow iron oxide, titanium oxide and talc are preferred.

Furthermore, one or more substance selected from the group consisting of yellow ferric oxide, titanium oxide and talc are preferred.

Besides, the polymer contained in the coating layer is preferably one or more substance selected from the group consisting of a cellulose-based polymer, an acrylic-based polymer and a vinyl-based polymer.

The cellulose-based polymer is preferably one or more substance selected from the group consisting of hypromellose, hydroxypropyl cellulose, carboxymethyl ethyl cellulose, hypromellose phthalate, hydroxypropyl methyl cellulose acetate succinate and ethyl cellulose.

In particular, hypromellose is preferred.

The acrylic-based polymer is preferably one or more substance selected from the group consisting of a methacrylic acid copolymer, an aminoalkyl methacrylate copolymer E and an aminoalkyl methacrylate copolymer RS.

The vinyl-based polymer is preferably one or more substance selected from the group consisting of polyvinyl alcohol, polyvinyl pyrrolidone, crospovidone and a polyvinyl alcohol/methyl methacrylate/acrylic acid copolymer.

It is preferable that the light-stabilizing substance contained in the coating layer is yellow ferric oxide, titanium oxide and talc and that the polymer is hypromellose.

Preferable aspects will be described below.

One aspect is a solid dosage form having a coating layer containing a light-stabilizing substance shielding or absorbing light of wavelength shorter than 450 nm wavelength and a polymer, and containing a compound represented by formula (I) or a pharmaceutically acceptable salt, thereof as the active ingredient, and particularly preferably a solid dosage form having a coating layer containing yellow ferric oxide, titanium oxide, talc and a polymer, and containing a compound represented by formula (I) or a pharmaceutically acceptable salt thereof as the active ingredient.

Another aspect is a solid dosage form having a coating layer containing a light-stabilizing substance and one or more polymers selected from the group consisting of a cellulose-based polymer, an acrylic-bated polymer and a vinyl-based polymer, and containing a compound represented by formula (I) or a pharmaceutically acceptable salt thereof as the active ingredient, preferably a solid dosage form having a coating layer containing a light-stabilizing substance shielding or absorbing light of wavelength shorter than 450 nm wavelength, and one or more polymers selected from the group consisting of a cellulose-based polymer, an acrylic-based polymer and a vinyl-based polymer, and containing a compound represented by formula (I) or a pharmaceutically acceptable salt thereof as the active ingredient, and more preferably a solid dosage form having a coating layer containing one or more light-stabilizing substances selected from the group consisting of a food tar dye, a food laked tar dye, a natural food dye, iron oxide, titanium oxide and talc, and one or more polymers selected from the group consisting of a cellulose-based polymer, an acrylic-based polymer and n vinyl-based polymer, and containing a compound represented by formula (I) or a pharmaceutically acceptable salt thereof as the active ingredient, and particularly preferably having a coating layer containing titanium oxide and talc, and one or more polymers selected from the group consisting of a cellulose-based polymer, an acrylic-based polymer and a vinyl-based polymer, and containing a compound represented by formula (I) or a pharmaceutically acceptable salt thereof as the active ingredient.

A still another aspect is a solid dosage form having a coating layer containing a light-stabilizing substance and a cellulose-based polymer, and containing a compound represented by formula (I) or a pharmaceutically acceptable salt thereof as the active ingredient, preferably having a coating layer containing a light-stabilizing substance shielding or absorbing light of wavelength shorter than 450 nm wavelength, and a cellulose-based polymer, and containing a compound represented by formula (I) or a pharmaceutically acceptable salt thereof as the active ingredient, and more preferably a solid dosage form having a coating layer containing one or more light-stabilizing substances selected from the group consisting of a food tar dye, a food laked tar dye, a natural food dye, iron oxide, titanium oxide and talc, and a cellulose-based polymer, and containing a compound represented by formula (I) or a pharmaceutically acceptable salt thereof as the active ingredient, and particularly preferably having a coating layer containing yellow ferric oxide, titanium oxide, talc and a cellulose-based polymer, and containing a compound represented by formula (I) or a pharmaceutically acceptable salt thereof as the active ingredient.

A still another aspect is a solid dosage form having a coating layer containing a light-stabilizing substance and hypromellose, and containing a compound represented by formula (I) or a pharmaceutically acceptable salt thereof as the active ingredient, preferably having a coating layer containing a light-stabilizing substance shielding or absorbing light of wavelength shorter than 450 nm wavelength, and hypromellose, and containing a compound represented by formula (I) or a pharmaceutically acceptable salt thereof as the active ingredient, and more preferably a solid dosage form having a coating layer containing one or more light-stabilizing substances selected from the group consisting of a food tar dye, a food laked tar dye, a natural food dye, iron oxide, titanium oxide and talc, and hypromellose, and containing a compound represented by formula (I) or a pharmaceutically acceptable salt thereof as the active ingredient, and particularly preferably having a coating layer containing yellow ferric oxide, titanium oxide, talc and hypromellose, and containing a compound represented by formula (I) or a pharmaceutically acceptable salt thereof as the active ingredient.

A still another aspect is a solid dosage form having a coating layer containing a light-stabilizing substance and a polymer, and containing monohydrochloride of compound represented by formula (I) as the active ingredient, preferably having a coating layer containing a light-stabilizing substance shielding or absorbing light of wavelength shorter than 450 nm wavelength, and a polymer, and containing monohydrochloride of compound represented by formula (I) as the active ingredient, and more preferably a solid dosage form having a coating layer containing one or more light-stabilizing substances selected from the group consisting of a food tar dye, a food laked tar dye, a natural food dye, iron oxide, titanium oxide and talc, and a polymer, and containing monohydrochloride of compound represented by formula (I) thereof as the active ingredient, and particularly preferably having a coating layer containing yellow ferric oxide, titanium oxide, talc and a polymer, and containing monohydrochloride of compound represented by formula (I) as the active ingredient.

Another aspect is a solid dosage form having a coating layer containing a light-stabilizing substance and one or more polymers selected from the group consisting of a cellulose-based polymer, an acrylic-based polymer and a vinyl-based polymer, and containing monohydrochloride of compound represented by formula (I) as the active ingredient, preferably a solid dosage form having a coating layer containing a light-stabilizing substance shielding or absorbing light of wavelength shorter than 150 nm wavelength, and one or more polymers selected from the group consisting of a cellulose-based polymer, an acrylic-based polymer and a vinyl-based polymer, and containing monohydrochloride of compound represented by formula (I) as the active ingredient, and more preferably a solid dosage form having a coating layer containing one or more light-stabilizing substances selected from the group consisting of a food tar dye, a food laked tar dye, a natural food dye, iron oxide, titanium oxide and talc, and one or more polymers selected from the group consisting of a cellulose-based polymer, an acrylic-based polymer and a vinyl-based polymer, and containing monohydrochloride of compound represented by formula (I) as the active ingredient, and particularly preferably having a coating layer containing yellow ferric oxide, titanium oxide and talc, and one or more polymers selected from the group consisting of a cellulose-based polymer, an acrylic-based polymer and a vinyl-based polymer, and containing monohydrochloride of compound represented by formula (I) as the active ingredient.

Another aspect is a solid dosage form having a coating layer containing a light-stabilizing substance and a cellulose-based polymer, and containing monohydrochloride of compound represented by formula (I) as the active ingredient, preferably a solid dosage form having a coating layer containing a light-stabilizing substance shielding or absorbing light of wavelength shorter than 450 nm wavelength, and a cellulose-based polymer, and containing monohydrochloride of compound represented by formula (I) as the active ingredient, and more preferably a solid dosage form having a coating layer containing one or more light-stabilizing substances selected from the group consisting of a food tar dye, a food laked tar dye, a natural food dye, iron oxide, titanium oxide and talc, and a cellulose-based polymer, and containing monohydrochloride of compound represented by formula (I) as the active ingredient, and particularly preferably having a coating layer containing yellow ferric oxide, titanium oxide and talc, and a cellulose-based polymer, and containing monohydrochloride of compound represented by formula (I) as the active ingredient.

Another aspect is a solid dosage form having a coating layer containing a light-stabilizing substance and hypromellose, and containing monohydrochloride of compound represented by formula (I) as the active ingredient, preferably a solid dosage form having a coating layer containing a light-stabilizing substance shielding or absorbing light of wavelength shorter than 450 nm wavelength, and hypromellose, and containing monohydrochloride of compound represented by formula (I) as the active ingredient, and more preferably a solid dosage form having a coating layer containing one or more light-stabilizing substances selected from the group consisting of a food tar dye, a food laked tar dye, a natural food dye, iron oxide, titanium oxide and talc, and hypromellose, and containing monohydrochloride of compound represented by formula (I) as the active ingredient, and particularly preferably having a coating layer containing yellow ferric oxide, titanium oxide and talc, and hypromellose, and containing monohydrochloride of compound represented by formula (I) as the active ingredient.

Even when the present formulation is packaged in an absorbing material or a shielding material against light of wavelength shorter than 450 nm wavelength, a color difference of the formulation caused under irradiation with light of a total irradiation amount of 1.2 million lux.hr is Δ20 or less, and the increased amount of the related substances including the E-form of the compound represented by formula (I) is 0.3% or less, from the beginning of the experiment. Besides, even when a formulation containing merely the compound represented by formula (I) is packaged in an absorbing material or a shielding material against light of wavelength shorter than 450 nm wavelength, a color difference of the formulation caused under irradiation with light of a total irradiation amount of 1.2 million lux.hr is Δ20 or less, and the increased amount of the related substances including the E-form of the compound represented by formula (I) is 0.3% or less, from the beginning of the experiment. As the light absorbing or shielding material, an aluminum or colored film may be used.

Any shape can be employed as the shape of the tablet, and specifically, the shape can be a circle, an ellipse, a sphere, a bar or a doughnut shape. Besides, the tablet may be a layered tablet, a dry coated tablet or the like, and is preferably a single layered tablet produced by a simple production method. Furthermore, the tablet may be provided with a mark or characters for improving identification, or a score line for splitting.

EXAMPLES

The present invention will be described in detail with reference to examples, comparative examples and reference examples, and it is noted that the present invention is not limited to these examples.

Example 1

Synthesis of Free Base A of the Compound Represented by Formula (I)

[Formula 19]

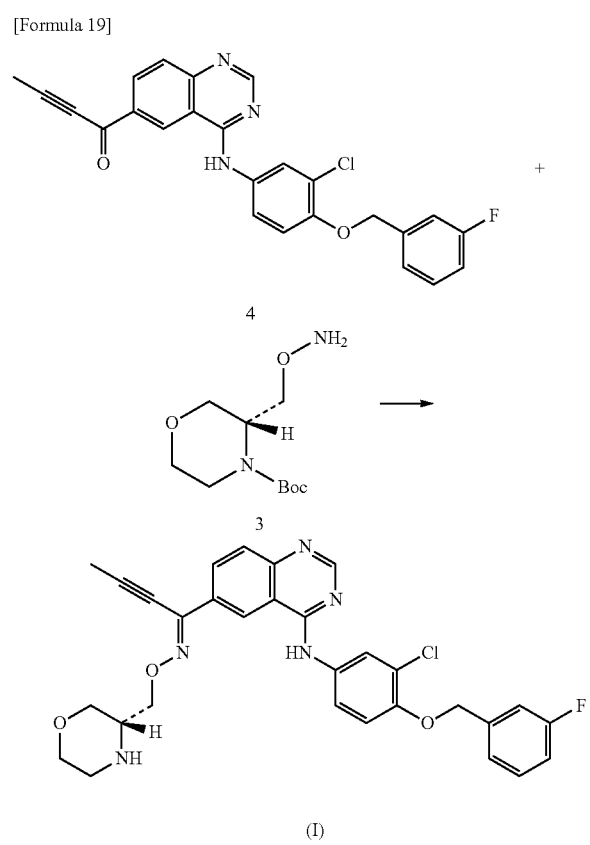

Compound 4 (8.23 g, 18.5 mmol) and Compound 3 (6.43 g, 27.7 mmol) were suspended in dioxane (326 mL), and a 2 mol/L solution (23.3 ml) of methanesulfonic acid in methanol was added. The mixture was stirred at 60° C. for 4 hours, then another portion or 2 mol/L methanesulfonic acid (14.1 mL) in methanol was added, and the mixture was stirred at 60° C. for 17 hours. The reaction solution was diluted with ethyl acetate (8.1.5 mL) and water (200 mL), and an aqueous potassium carbonate solution (20.65 g of potassium carbonate, 150 mL of water) was added for extraction. The organic layer was washed with saline (50 mL of brine, 250 mL of water). Then, the organic layer was dried over magnesium sulfate and filtered, then the filtrate was concentrated, and thus free base A (11.83 g) of the compound represented by formula (I) was obtained as brown oil.

Example 2

Synthesis of Free Base B of the Compound Represented by Formula (I)

Free base A (6.88 g) synthesized using Compound 4 (4.94 g) according to the synthesis method of free base A of the compound represented by formula (I) was dissolved in methanol (28 mL), and a 4 mol/L solution (2.5 mL) of hydrochloric acid in ethyl acetate was added. Stirring the mixture at room temperature for 2 hours yielded precipitates. The mixture was diluted with ethyl acetate (50 mL), and methanol was distilled off under reducer pressure. This operation was repeated, and the mixture was further diluted with ethyl acetate (30 mL) and stirred at room temperature for 30 minutes. The resulting solids were filtered, washed with ethyl acetate (30 mL), and dried, and thus monohydrochloride (5.04 g) of the compound represented by formula (I) was obtained. Then, 3.00 g of the monohydrochloride was suspended in ethyl acetate (50 mL), an aqueous potassium carbonate solution (1.04 g of potassium carbonate, 15 mL of water) was added at 0° C., and the mixture was extracted with ethyl acetate. The extract was washed with brine, dried over anhydrous sodium sulfate, and filtered, and then the filtrate was concentrated under reduced pressure. Diethyl ether (24 mL) and hexane (6 mL) were added to the residue, the resulting solids were washed with a mixed solution of hexane-diethyl ether (1:1), and thus free base B (2.63 g) of the compound represented by formula (I) was obtained as pale yellow solids.

Example 3

Synthesis of Monohydrochloride Crystalline Form I of the Compound Represented by Formula (I)

After free base A (1.18 g) of the compound represented by formula (I) was dissolved in ethyl acetate (8 mL) and filtered, the filtrate was concentrated under reduced pressure to a half volume, and a 4 mol/L solution (0.42 mL) of hydrochloric acid in ethyl acetate was added. Diethyl ether (2 mL) was added, and the resulting precipitates were filtered and washed with a mixed solution of diethyl ether:ethyl acetate (2:3) and then diethyl ether. Solids (817 mg) collected by filtration were dissolved in methanol (20 mL) under warming, concentrated under reduced pressure to a total amount of 3.6 g, and left to stand at room temperature. Precipitates were filtered, washed with cold methanol and then diethyl ether and dried, and thus monohydrochloride crystalline form I (701 mg) of the compound represented by formula (I) was obtained as yellow crystals.

(NMR and Elemental Analysis)

NMR data are shown, there are cases where all peaks measured are not described. The NMR data of the monohydrochloride crystalline form I of the compound of the compound represented by formula (I) are shown below.

$^1$H-NMR (300 MHz, DMSO-d6) δ 2.28 (6H, s), 3.08-3.28 (2H, m), 3.58-3.75 (3H, m), 3.90-3.94 (1H, m), 4.03 (1H, dd, J=12, 2.7 Hz), 4.44 (2H, d, J=5.4 Hz), 6.27 (2H, s), 7.15-7.22 (1H, m), 7.26-7.35 (3H, m), 7.44-7.51 (1H, m), 7.72 (1H, dd, J=9.0, 2.4 Hz), 7.82 (1H, d, J=8.7 Hz), 7.99 (1H, d, J=2.4 Hz), 8.26 (1H, dd, J=8.7, 1.8 Hz), 8.60 (1H, s), 8.88 (1H, d, J=1.5 Hz), 9.29 (1H, s), 10.20 (1H, s).

In addition, the calculated and actual values of elemental analysis of monohydrochloride crystalline form I of the compound of the compound represented by formula (I) are shown below.

calculated value: C, 60.41; H, 4.73; Cl, 11.89; F, 3.19; N, 11.74 measured value: C, 60.17; H, 4.79; Cl, 11.62; F, 3.06; N, 11.81

(Measurement of X-ray Powder Diffraction Pattern)

Data of X-ray powder diffraction measurement of the obtained crystals in each Example is obtained according to X-ray powder diffraction analysis method in General tests in Japanese Pharmacopoeia as following conditions:
(Method A)
(Device)
D-8 Discover by Bruker
(Operation method)
Samples were measured under the following conditions.
Measuring method: Reflection method
Light source: Cu tube
Wavelength used: CuKα ray
Tube current: 40 mA
Tube voltage: 40 kV
Sampling plate: Glass, aluminum
X-ray incident angle: 3-40°

The results of X-ray powder diffraction of monohydrochloride crystalline form I of the compound of the compound represented by formula (I) obtained in Example 1 are shown in Table 1. (Measurement conditions: Method A)

TABLE 1

| 2θ |
|---|
| 6.838 |
| 7.982 |
| 14.122 |
| 17.941 |
| 18.451 |
| 20.569 |
| 20.989 |
| 22.528 |
| 25.843 |
| 28.409 |

Example 4

Synthesis of Monohydrochloride Crystalline Form I of the Compound Represented by Formula (I)

After free base A (1.18 g) of the compound represented by formula (I) was dissolved in ethyl acetate (8 mL) and filtered, the filtrate was concentrated under reduced pressure to a half volume, and a 4 mol/L solution (0.42 mL) of hydrochloric acid in ethyl acetate was added. Diethyl ether (2 mL) was added, and the resulting precipitates were filtered and washed with a mixed solution of diethyl ether:ethyl acetate (2:3) and then diethyl ether. Solids (817 mg) collected by filtration were dissolved in methanol (20 mL) under warming, concentrated under reduced pressure to a total amount of 3.6 g, and left to stand at room temperature. Precipitates were filtered, washed with cold methanol and then diethyl ether and dried, and thus monohydrochloride crystalline form I (701 mg) of the compound represented by formula (I) was obtained as yellow crystals.

The results of X-ray powder diffraction of monohydrochloride crystalline form I of the compound represented by formula (I) obtained in Example 3 are shown in Table 2. (Measurement conditions: Method A)

TABLE 2

| $2\theta$ |
|---|
| 7.906 |
| 9.734 |
| 11.933 |
| 15.791 |
| 18.532 |
| 23.919 |
| 25.912 |
| 26.208 |
| 26.728 |
| 28.399 |

Example 6

Synthesis of Dihydrochloride Crystal of the Compound Represented by Formula (I)

First, to 16 g of the ethanol solution (about 400 g) containing the free base (about 50 g) of the compound represented by formula (I), the monohydrochloride crystalline form I (2.5 mg) obtained in Example 3 was added, and then 0.838 g (2.5 eq) of concentrated hydrochloric acid was added. The mixture was stirred for 2 hours, then the precipitated solids were collected by filtration, and thus dihydrochloride crystals of the compound represented by formula (I) were obtained.
Elemental analysis:
Calculated value: C, 57.59; H, 4.64; Cl, 15.87: F, 3.04; N, 11.19 (1.8 HCl salt)
Measured value: C, 57.99; H, 5.51; Cl, 16.74; F, 2.86; N, 11.47

The results of X-ray powder diffraction of dihydrochloride crystals of the compound represented by formula (I) are shown broad peaks, and it was thus found that dihydrochloride crystals of the compound represented by formula (I) have low crystallinity.

In general, low crystallinity crystals are known to have poor physical stability, poor chemical stability, and such features, and it is said that the handling of such an active pharmaceutical ingredient is difficult (Reference: Recent Progress in Physicochemical Characterization and Formulation Technologies for Poorly Soluble Drugs, 2010, pp. 215-216). For example, in the case of using low crystallinity crystals as an active ingredient, they may transition to crystals that have good crystallinity when synthesis is carried out in a large scale. Also, due to poor stability, they are not suitable for long-term storage.

Various crystals of monohydrochloride of the compound represented by formula (I) are crystals having good crystallinity, and it was thus found that forming the compound represented by formula (I) into monohydrochloride provides crystalline forms suitable for an active pharmaceutical ingredient.

From above, it was found that monohydrochloride crystals of the compound represented in any crystalline form have good crystallinity and are in crystalline forms suitable for use as an active pharmaceutical ingredient of a drug.

Example 6

Test of Solubility in Water for Injection
1. Formulation of Calibration Curve

First, 5 mg of monohydrochloride crystalline form I of the compound represented by formula (I) was precisely weighed and dissolved in a mixed solution of acetonitrile:water (1:1), and thus a 500 µg/mL solution was obtained. The obtained solution was diluted with a mixed solution of acetonitrile: water (1:1) such that the concentrations of the compound were 5 and 50 µg/mL, and a standard calibration curve was prepared. The same operation was carried out for monohydrochloride crystalline form II, monohydrochloride crystalline form V, monohydrochloride crystalline form VI, mono-p-toluenesulfonate crystalline form I, and free base crystals.

2. Formulation of Sample Solution

First, 1 mg of monohydrochloride crystalline form I of the compound represented by formula (I) was precisely weighed and transferred to a vial having a volume of 4 mL. Then, 1 mL of water (water for injection) was added, and the mixture was stirred at 37° C. for 1 hour. After being stirred, this suspension was filtered, and the peak area using a solution obtained by diluting the filtrate two-fold with a mixed solution of acetonitrile:water (1:1) as a sample. The concentration was calculated using the peak area and the calibration curve prepared above. The same operation was carried out for monohydrochloride crystalline form II, monohydrochloride crystalline form V, monohydrochloride crystalline form VI, mono-p-toluenesulfonate crystalline form I, and free base crystals.

(Results)

The respective solubilities of the monohydrochloride crystalline form I, monohydrochloride crystalline form II, monohydrochloride crystalline form V, monohydrochloride crystalline form VI, mono-p-toluenesulfonate crystalline form I, and free base crystals of the compound represented by formula (I) in water for injection are shown in Table 3.

TABLE 3

| | Free base crystal | Monohydrochloride crystalline form I | Monohydrochloride crystalline form II | Monohydrochloride crystalline form V | Monohydrochloride crystalline form VI | Mono-p-toluenesulfonate-crystalline form I |
|---|---|---|---|---|---|---|
| Water for injection | N.D. | 34.5 | 56.0 | 14.0 | 12.9 | 26.6 |

(N.D.: Not Detected, Unit: µg/mL)

As is clear from the above table, the free base crystals of the compound represented by formula (I) was not dissolved in water for injection at all but, on the other hand, the monohydrochloride crystalline form I, monohydrochloride crystalline form II, monohydrochloride crystalline form V, monohydrochloride crystalline form VI, and mono-p-toluenesulfonate crystalline form I of the compound represented by formula (I) showed high solubilities in water for injection.

In general, the solubility of a pharmaceutical agent is deeply involved in disposition, and an active pharmaceutical ingredient is desired to have high solubility. Accordingly, it was found that the monohydrochloride crystalline form I, monohydrochloride crystalline form II, monohydrochloride crystalline form V, monohydrochloride crystalline form VI, and mono-p-toluenesulfonate crystalline form I of the compound represented by formula (I) have high solubilities, and are in crystalline forms suitable for use as an active pharmaceutical ingredient of a drug.

Example 7

Test of Solubility in Organic Solvent

The monohydrochloride crystalline form I, monohydrochloride crystalline form V, and free base crystals of the compound represented by formula (I) were each suspended in 2-propanol, acetone, and ethyl acetate, and stirred at 22° C. for 4 hours, and the concentrations of supernatants were measured.

(Results) Solubilities in 2-propanol, acetone, and ethyl acetate are shown in Table 4.

TABLE 4

| Sample | Concentration (% by weight) | | |
|---|---|---|---|
| | 2-Propanol | Acetone | Ethyl acetate |
| Monohydrochloride crystalline form I | 0.03 | 0.08 | 0.01 |
| Monohydrochloride crystalline form V | 0.01 | 0.02 | 0.00 |
| Free base crystal | 0.49 | 8.1 | 3.3 |

As is clear from Table 20, it can be understood that the concentrations (% by weight) of the free base crystals of the compound represented by formula (I) in various organic solvents are high (about 0.5% by weight to about 8% by weight), showing high solubility, but, on the other hand, the monohydrochloride crystalline form I and the monohydrochloride crystalline form V of the compound represented by formula (I) barely dissolve in various organic solvents (both 0.1% by weight or less). That is to say, when synthesizing the compound represented by formula (I), if the produced the compound represented by formula (I) has high solubility in organic solvents, the ratio of the product precipitated from organic solvents is small, and the yield is reduced. Accordingly, it was found that the monohydrochloride crystalline form I and the monohydrochloride crystalline form V of the compound represented by formula (I) are in crystalline forms suitable for use as an active pharmaceutical ingredient of a drug.

Example 8

Purification Effect by Crystallization

Purification effects of the free base crystals, monohydrochloride crystalline form I, and monohydrochloride crystalline form VI of the compound represented by formula (I) crystallized from an ethyl acetate solution of the compound represented by formula (I) were compared respectively.

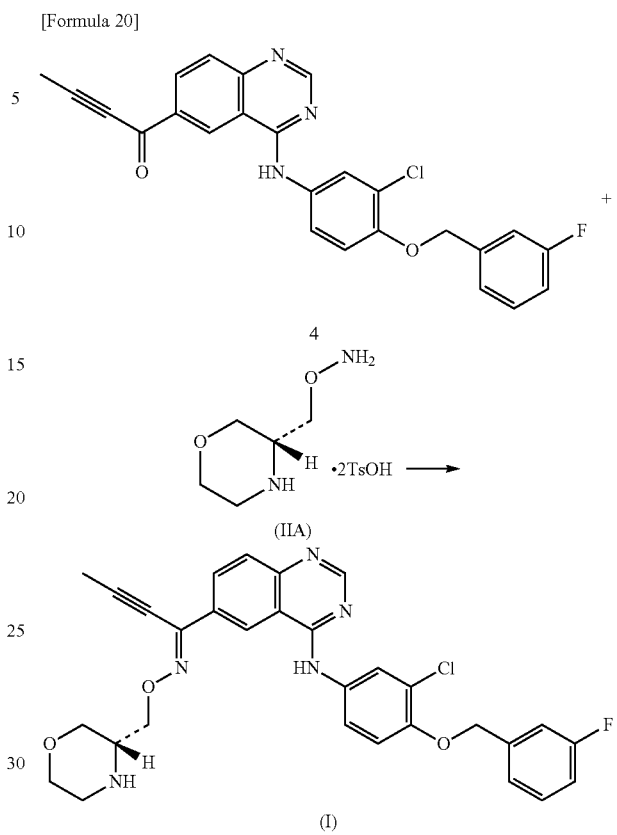

(Step 1) Synthesis of Ethyl Acetate Solution of the Compound Represented by Formula (1)

Compound 4 (30.04 g, 77.4 mmol) was dissolved in N-methylpyrrolidone (70.86 g) and tetrahydrofuran (18.68 g), added to a slurry of Compound (IIA) (30.85 g, 77.3 mmol), p-toluenesulfonic acid monohydrate (15.37 g, 80.8 mmol), tetrahydrofuran (53.41 g), and water (5.40 g), and stirred at 57° C. for 5 hours. After the mixture was cooled to room temperature, Compound 4 (0.25 g) was added. Thereafter, the pH was adjusted to 9.0 with an aqueous sodium hydroxide solution, followed by extraction with ethyl acetate (651.52 g). The extract was concentrated to 107.39 g, ethyl acetate (162.40 g) was added, and thus an ethyl acetate solution (269.76 g) of the compound represented by formula (I) was obtained.

(Step 21) Synthesis of Free Base Crystals of the Compound Represented by Formula (I)

The ethyl acetate solution (89.92 g) of the compound represented by formula (I) was concentrated to 22.97 g, heptane (17.67 g) and ethyl acetate (13.27 g) were added, then the mixture was heated to 60° C. and thus solids were precipitated. Ethyl acetate (12.31 g) was added, the mixture was cooled to room temperature, heptane (41.26 g) and ethyl acetate (6.0 g) were added, and the mixture was concentrated to 49.70 g. Heptane (49.83 g) and ethyl acetate (27.0 g) were added, the mixture was left to stand overnight and then filtered, and thus free base crystals (10.91 g, 86.7%) of the compound represented by formula (I) were obtained.

(Step 2-2) Synthesis of Monohydrochloride Crystalline Form I of the Compound Represented by Formula (I)

Water (0.13 g) and 2-propanol (16.26 g) were added to the ethyl acetate solution (40.72 g) of the compound represented by formula (I), and the mixture was heated to 45° C. Seed crystals (225.7 mg) of crystalline form I was added, and then the pH was adjusted to 4.07 with 35% hydrochloric acid. The mixture was stirred a 25° C. for about 30 minutes and then filtered, and thus monohydrochloride crystalline form I (5.50 g, 90.6%) of the compound represented by formula (I) was obtained.

(Step 2-3) Synthesis of monohydrochloride crystalline form VI of the compound represented by formula (I)

2-Propanol (7.85 g) was added to the ethyl acetate solution (45.20 g) of the compound represented by formula (I), and the mixture was heated to 60° C. The pH was adjusted to 8.5 with 35% hydrochloric acid, then the mixture was stirred at 25° C. for about 30 minutes and filtered, and thus monohydrochloride crystalline form VI (5.84 g. 86.7%) of the compound represented by formula (I) was obtained.

The qualities of the free base crystals, monohydrochloride crystalline form I, and monohydrochloride crystalline form VI of the compound represented by formula (1) obtained by the above synthesis methods were evaluated using HPLC.

TABLE 5

| Sample | Impurity A | Impurity B | E isomer | Compound (I) | Impurity C |
|---|---|---|---|---|---|
| | \multicolumn{5}{c}{Retention time} | | | | |
| | 20 min | 21 min | 38 min | 44 min | 62 min |
| Pre-crystallization solution (Ethyl acetate solution) | 0.31 | 0.12 | 6.26 | 89.38 | 0.74 |
| Free base crystal | 0.12 | 0.05 | 1.29 | 97.81 | 0.67 |
| Monohydrochloride crystalline form I | 0.16 | 0.03 | 1.00 | 98.44 | 0.27 |
| Monohydrochloride crystalline form VI | 0.02 | N.D. | 0.80 | 99.17 | N.D. |

(N.D.: Not Detected, Unit: Area %)

When the purities of the respective crystals obtained above are compared, as is clear from Table 21, it can be understood that in order of monohydrochloride crystalline form VI, monohydrochloride crystalline form I, and free base crystals, the ratio of the peak area % of the compound represented by formula (I) is larger (about 99.2%, about 98.4%, and about 97.8%, respectively), and the amount of various impurities contained is smaller. Accordingly, it was found that when performing crystallization from a pre-crystallization solution (an ethyl acetate solution) containing large amounts of impurities, it is possible to remove various impurities and obtain crystals having a higher purity by obtaining crystals as monohydrochloride crystalline form VI or monohydrochloride crystalline form I than obtaining crystals as free base crystals.

In general, for crystals containing large amounts of impurities, it is necessary to repeat the recrystallization step to increase the purity of the crystals. When the recrystallization step is repeated, the amount of crystals elute into the mother liquor is increased, thus resulting in a reduced yield. Depending on the impurity, the ratio of the impurity removed by the recrystallization step is small, and therefore it is often the case that the purity cannot be increased by repeating the recrystallization step a practical number of times.

Accordingly, it can be said that the monohydrochloride crystalline form VI and the monohydrochloride crystalline form I of the compound represented by formula (I) are in crystalline forms suitable for scale-up synthesis because high-purity crystals can be obtained by single crystallization. That is to say, it was found that the monohydrochloride crystalline form VI and the monohydrochloride crystalline form I of the compound represented by formula (I) are in crystalline forms suitable for use as an active pharmaceutical ingredient of a drug.

Example 9

Water Sorption-desorption Isothermal Measurement

Table C shows the ratios of increased moisture mass of the monohydrochloride crystalline form I, monohydrochloride crystalline form V, monohydrochloride crystalline form VI, free base crystals, mono-p-toluenesulfonate crystals, and monosulfate crystals of the compound represented by formula (I).

TABLE 6

| | Ratio of increased mass |
|---|---|
| Monohydrochloride crystalline form I | About 0.8% |
| Monohydrochloride crystalline form II | About 0.3% |
| Monohydrochloride crystalline form V | About 1.7% |
| Monohydrochloride crystalline form VI | About 0.5% |
| Mono-p-toluenesulfonate crystalline form I | About 1.4% |
| Free base crystal | About 1.0% |
| Monosulfate crystal | About 3.3% |

As is clear from Table 22, it was found that the monosulfate crystals of the compound represented by formula (I) exhibited a moisture increase of about 3.3% but, on the other hand, the ratios of moisture increase of the monohydrochloride crystalline form I, monohydrochloride crystalline form H, monohydrochloride crystalline form V, monohydrochloride crystalline form VI, and mono-p-toluenesulfonate crystalline form I of the compound represented by formula (I) were small.

In general, it is considered that salt crystals are more likely to be influenced by moisture absorption, and absorptivity is said to vary depending on the type of salt (Reference: Recent Progress in Physicochemical Characterization and Formulation Technologies for Poorly Soluble Drugs, 2010, pp. 117-118). Also, crystals that are likely to adsorb water undergo deliquescence and like a phenomenon, and it is difficult to handle such crystals. Moreover, such crystals are not suitable for long-term storage and are rarely selected as an active pharmaceutical ingredient. Accordingly, it was found that the monohydrochloride crystalline form I, monohydrochloride crystalline form II, monohydrochloride crystalline form V, monohydrochloride crystalline form VI, and mono-p-toluenesulfonate crystalline form I of the compound represented by formula (I) are in crystalline forms suitable for use as an active pharmaceutical ingredient of a drug because the ratios of moisture increase are small.

Example 9

Light Exposure Test

Table 7 shows the results of a light exposure test of the monohydrochloride crystalline form I, monohydrochloride crystalline form II, monohydrochloride crystalline form V, monohydrochloride crystalline form VI, and mono-p-toluenesulfonate crystalline form I of the compound represented by formula (I).

TABLE 7

| Sample | E isomer (Retention time 38 minutes)* | | |
|---|---|---|---|
| | Dark control | Light exposed sample | Increased amount |
| Monohydrochloride crystalline form I | 0.63 | 4.41 | 3.78 |
| Monohydrochloride crystalline form II | 1.44 | 1.21 | −0.23 |
| Monohydrochloride form crystal V | 0.13 | 1.19 | 1.06 |
| Monohydrochloride form crystal VI | 1.16 | 1.80 | 0.64 |
| Free base crystal | N.D. | 2.59 | 2.59 |
| Mono-p-toluenesulfonate crystalline form I | 0.10 | 32.86 | 32.76 |

(The unit is area %. *Concerning other peaks, changes due to light exposure are barely recognised.)

As shown in Table 7, when the monohydrochloride crystalline form I, monohydrochloride crystalline form II, monohydrochloride crystalline form V, and monohydrochloride crystalline form VI of the compound represented by formula (I) were subjected to a light exposure test, conversion from a Z isomer to an E isomer was barely observed, or an increase was only as much as about 3.8%. On the other hand, it was found that the photostability of the mono-p-toluenesulfonate crystalline form I of the compound represented by formula (I) is poor because the E isomer increases about 33% after light exposure.

In general, crystals having poor photostability undergo decomposition and like a phenomenon due to light, and unacceptable changes may occur due to light exposure. Also, such crystals require utmost attention to the storage method, and it is difficult to handle such crystals.

Accordingly, it was found that the monohydrochloride crystalline form I, monohydrochloride crystalline form II, monohydrochloride crystalline form V, and monohydrochloride crystalline form VI of the compound represented by formula (I) are in crystalline forms suitable for use as an active pharmaceutical ingredient of a drug because light stability under light exposure conditions is good.

Example 11

Influence of Light of the Compound Represented by Formula (I)

In order to research the influence of light of the compound represented by formula (I), the amount of the related substances was measured after illumination with constant quantity of light.

a. Method for Light Irradiation Experimental

A fixed amount of monohydrochloride of the compound represented by formula (I) was collected and dissolved in a mix of pH7 buffer:methanol:acetonitrile=38:31:31 to prepare a solution of 800 μg/mL. The solution was sealed in glass bottles. Thereafter, the glass bottles containing solution were irradiated with light of different wavelengths by a light irradiator (CRM-FA manufactured by Nippon Spectroscopy) and the amounts of related substances were measured.

b. Method for Measuring the Related Substances

The amount of the related substances was measured by liquid chromatography by employing the following method and conditions. The main related substance was the E-form of the optical isomer of the compound represented by formula (I). Therefore, in the analysis of the related substance amount, the E-form of the optical isomer of the compound represented by formula (I) was used as a reference for the analysis.

Detector: ultraviolet absorptiometer (measurement wavelength: 225 nm)
Column: Cadenza CW-C18 3μ, 4.6×150 mm (Imtakt)
Column temperature: constant temperature around 35° C.
Mobile Phase A: 10 mM ammonium acetate,
Mobile Phase B: acetonitrile/methanol mixture
Delivery of mobile phase: controlled for a concentration gradient with a mixing ratio between the mobile phase A and the mobile phase B changed as shown in Table 8

TABLE 8

| Time after Injection (min) | Mobile Phase A (vol %) | Mobile Phase B (vol %) |
|---|---|---|
| 0.0-40.0 | 47 | 53 |
| 40.0-60.0 | 47 1-80.10 | 53 1-80.00 |
| 60.0-05.0 | 10 1-80.47 | 90 1-80.53 |
| 65.0-65.1 | | |
| 65.1-80.0 | | |

Flow rate: about 1.0 mL/min (retention time of compound represented by formula (I): 28 minutes)
Injection amount: 100 μL
Sample cooler temperature: about 5° C.
Washing solution for autoinjector: acetonitrile/methanol mixture (1:1)
Range of area measurement: 65 minutes after injection of sample solution
Equation for calculating amount of related substances:

$$\text{amount of each 1 related substance (\%)} = \frac{A_{Ti}}{\Sigma A_T} \times 100$$

$$\text{Total amount of total related substance (\%)} = \frac{\Sigma A_{Ti}}{\Sigma A_T} \times 100$$

$A_{Ti}$: peak area of each related substance in sample solution
$\Sigma A_T$: Sum of peak areas of sample solution (excluding blank and system peaks)
$\Sigma A_{Ti}$: Sum of peak areas of each related substances of sample solution c. Result The changes in the amount of related substances due to different wavelengths of light are shown in. The FIGURE. As a result, if the wavelength of light was shorter than 450 nm, the total amount of related substances increased as the wavelength decreased. However, if the wavelength of light was higher than 450 nm, the total amount of related substances increased little, even at higher wavelengths.

Example 12

Formulation of Tablets and Measurement of Related Substance Amount and Odor Difference by Light Irradiation
a. Formulation of Uncoated Tablets A formulation per uncoated tablet which not coating with a light-stabilizing substance and a polymer of the present invention is shown in Table 9. Monohydrochloride of the compound represented by formula (I), D-mannitol (Rockett), crystalline cellulose (Asahi Kasei Co., Ltd.) and some calmelose calcium (nitilin chemistry) were mixed in the bag, and the mixture was added into stir-mixing machine (Type 10 high-speed mixer, Shenjiang Industrial Co., Ltd.). After charging, an aqueous solution of 10% by weight of hydroxypropyl cellulose (Shin-Etsu Chemical) was sprayed and granulated in a stirred granulating. The granulation conditions of the agitated granulator, the drying of the granulate, and the conditions of granulation are as follows:
(Conditions for Agitated Granulating)
  Rotational Speed of Agitator: 240 rpm
  Rotational Speed of Chopper: 2000 rpm
  Pre-granulating mixing time: 0.5 min
  Acceleration in Solution Injection: 120 mL/min (60 mL/min at two locations)
  Drying Conditions of Granulate: WSG2 & 5 Type Fluidized Bed Granulator
    (Air supply temperature setting: 70° C. drying end point: drying for 30 minutes)
  Granulating conditions for granules: P-3 power mill (Basket: 20 mesh, rotation number: 3000 rpm).

The obtained granules, the remaining calcium carmelose and magnesium stearate were mixed in a bag, and these mixtures were compressed by a tablet machine (RTM-S30K-2S type tablet machine, Kikusui Works) to produce tablets having diameters of 8 mm. The conditions for tableting are as follows;
  Tablets with a rotation rate of 30 rpm and three rod-shaped molars, using a tableting machine RTM-S30K-2S

TABLE 9

| Composition | Amount (mg) |
|---|---|
| Compound represented by Formula (I) | 100 |
| D-mannitol | 15 |
| Macrocrystalline cellulose | 40 |
| hydroxypropyl cellulose | 6 |
| calmelose calcium | 18 (10 inside granules, 8 outside granules) |
| magnesium stearate | 2 |
| Total | 211 | b. Method for Formulation of Coated Tablet

The amounts of coating layer on uncoated tablet per tablet, such as a light-stabilizing substance (titanium oxide (Freund's Corp.), yellow iron trioxide (Tatsumi Chemicals), talc (Merck) and macromolecules (Hypromellose (Shinte Chemicals)) of the present formulation are shown in Table 10, and the amounts of coating layer on uncoated tablet per tablet unit area are shown in Table 11, respectively. These a light-stabilizing substance and a polymer were dissolved in purified water to make 10% concentrations of coating solution, and uncoated tablets were coated under the following coating conditions. The surface area of tablets was 156.6 mm$^2$.

The uncoated tablets of Table 9 were put into approximately 1000 g Labo Coater HC-LABO (Freund Corp.) and coated with the photostabilizing substances and macromolecules described in Table 10 at the following coating conditions. The conditions for coating:
  Charged amount: about 1000 g
  Coating machine: Labo Coater HO-LABO (Freund Corp.)
  Spray gun: 70 SS
  Nozzle diameter: 1.3 mm
  Flow rate of sprayed air: about 50 L/min
  Spray distance: 20 cm
  Rotational speed of pan: 24 rpm
  Temperature of supplied air: 60° C.
  Static pressure in the pan: −50 Pa
  Flow rate of supplied air: 1.0 m$^3$/min

TABLE 10

| Unit (mg) | Comparative Example 1 | Example 1 | Example 2 | Example 3 | Example 4 |
|---|---|---|---|---|---|
| Hypromellose | 0 | 3.02 | 5.21 | 5.49 | 8.50 |
| Titanium oxide | 0 | 0.88 | 1.52 | 1.60 | 2.49 |
| Yellow ferric oxide | 0 | 0.09 | 0.16 | 0.17 | 0.26 |
| Talc | 0 | 0.30 | 0.52 | 0.55 | 0.85 |
| Total | 0 (0%) *[1] | 4.29 (2.2%) | 7.41 (3.8%) | 7.81 (4.0%) | 12.1 (6.2%) |
| Total amount of titanium oxide + yellow iron trioxide + talc | 0 | 1.27 | 2.20 | 2.32 | 3.60 |

*[1] % in ( ) is the weight % of the total amount of hypromellose, titanium oxide, yellow iron trioxide and talc relative to plain tablets.

TABLE 11

| Unit (mg/mm$^2$) | Comparative Example 1 | Example 1 | Example 2 | Example 3 | Example 4 |
|---|---|---|---|---|---|
| Titanium oxide | 0 | 0.00562 | 0.00971 | 0.01022 | 0.01591 |
| Yellow ferric oxide | 0 | 0.00058 | 0.00102 | 0.00109 | 0.00166 |
| Talc | 0 | 0.00192 | 0.00332 | 0.00351 | 0.00543 |
| Total amount of titanium oxide + yellow iron trioxide + talc | 0 | 0.00812 | 0.01405 | 0.01482 | 0.02300 | c. Light Irradiation Experimental Method and Method for Measuring the Related Substances Tablets coated with a coating layer of table 10 were irradiated with light. The tablets were cleaned into a light irradiator (LTL-400D5, Nagano Science) and irradiated with a total light radiation amount of 1.2 million lux.hr. Related substances were extracted from the tablets after light irradiation, and the amount of related substances was determined by the above-mentioned measurement method of related substances.

d. Method for Measuring Color Difference

The tablets coated with the coating layer of Table 10 were irradiated with light in the above light irradiation experimental method, and the color difference of the tablets was measured by the color difference measurement method.

e. Result

The amount of related substances in the tablets of Formulations Comparative Example 1 and Examples 1 to 4 after irradiation with light is shown in Table 12. As a result, the amount of the related substance after light irradiation was high in the formulation comparative example 1 without the coating layer, and the amount of the related substance increased from the start of the experiment was 0.34%. On the other hand, in formulation Examples 1 to 4 with a coating layer containing a photostabilizer and a polymer, the amount of related substances increased was low, and the amount of related substances increased from the start of the experiment was not more than 0.3%, and the amount of related substances generally decreased as the amount of photostabilizer substances per unit area of the tablet was higher. Therefore, it was revealed that the amount of the related substances of the compounds indicated by formula (I) can be reduced by providing a coating layer on the surface of plain tablets containing photostabilizing substances and macromolecules.

Table 13 shows the color difference of the tablets after light irradiation with respect to the tablets of formulation Comparative Example 1 and formulation Examples 1 to 4. As a result, it was obvious that in the formulation comparative Example 1 without the coating layer, the color difference after light irradiation was obviously high, and the color of the formulation also changed according to the human eye. On the other hand, in formulation Example 1 to 4 with a coating layer containing a photostabilizing substance and a polymer, the variation of the color difference was small, and the color difference was Δ20 or less. Furthermore, the more the amount of coverage layer, the more generally the variation of color difference was reduced. Therefore, it was revealed that the color difference of the formulation containing the compound indicated by formula (I) could be reduced by providing a coating layer containing a photostabilizing material and a polymer on the surface of plain tablets.

TABLE 12

|  | Comparative Example 1 | Example 1 | Example 2 | Example 3 | Example 4 |
|---|---|---|---|---|---|
| Total amount the related substances (%) before the start of light irradiation (1) | 0.34 | 0.34 | 0.33 | 0.33 | 0.33 |
| Total amount of the related substances (%) after total light irradiation dose of 1.2 million lux · hr (2) | 0.68 | 0.48 | 0.38 | 0.39 | 0.34 |
| Differences (%) in the amount of the related substances of (2) − (1) | 0.34 | 0.14 | 0.05 | 0.06 | 0.01 |

TABLE 13

|  | Comparative Example 1 | Example 1 | Example 2 | Example 3 | Example 4 |
|---|---|---|---|---|---|
| Color difference of tablets after irradiation with total light dose of 1.2 million lux · hr | 24.19 | 2.62 | 1.10 | 1.15 | 0.60 |

INDUSTRIAL APPLICABILITY

It was found that a novel finding that the formulation containing the compound represented by formula (I) in which the amount of the related substances increased, and moreover, the color difference of the formulation becomes high under light irradiation. Therefore, the amount of related substance decreased and the color difference of the formulation could be reduced by coating the surface of the preparation with a light-stabilizing substance and a polymer. In this manner, the formulation containing the compound represented by formula (I) can be stably stored under irradiation with light.

The invention claimed is:

1. A solid dosage form comprising a coating layer comprising a light-stabilizing substance and a polymer, and a compound represented by formula (I):

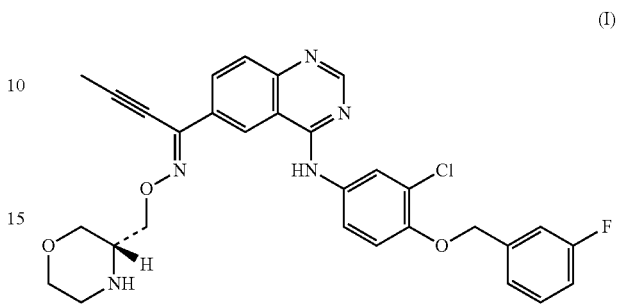

(I)

or its pharmaceutically acceptable salt as an active ingredient.

2. The solid dosage form according to claim 1, wherein the light-stabilizing substance in the coating layer is a substance that shields or absorbs light of wavelength shorter than 450 nm wavelength.

3. The solid dosage form according to claim 1, wherein the light-stabilizing substance in the coating layer is at least one substance selected from the group consisting of edible tar dye, edible lake tar dye, edible natural dye, ferric oxide, titanium oxide and talc.

4. A solid dosage form comprising a coating layer comprising at least one substance selected from the group consisting of edible tar dye, edible lake tar dye, edible natural dye, ferric oxide, titanium oxide and talc, and a polymer, and a compound represented by formula (I):

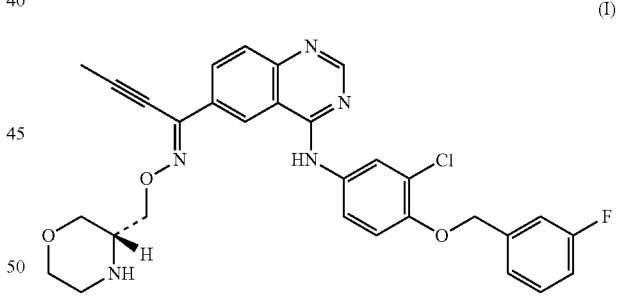

(I)

or its pharmaceutically acceptable salt as an active ingredient.

5. The solid dosage form according to claim 1, wherein the polymer in the coating layer is at least one substance selected from the group consisting of a cellulose-based polymer, an acrylic polymer and a vinyl polymer.

6. The solid dosage form according to claim 1, wherein the light-stabilizing substance in the coating layer comprises ferric oxide, titanium oxide and talc, and the polymer in the coating layer is cellulose-based polymer.

7. A solid dosage form comprising a coating layer comprising ferric oxide, titanium oxide, talc and a cellulose-based polymer, and a compound represented by formula (I):

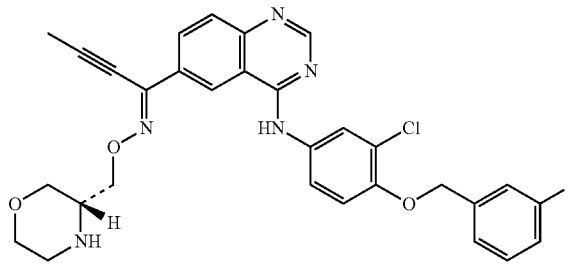

or its pharmaceutically acceptable salt as an active ingredient.

8. The solid dosage form according to claim 1, wherein an increased amount of substances related to the compound represented by formula (I), including the E-form of the compound represented by formula (I), is 0.3% or less, from the beginning of an experiment, when irradiated with light in a total irradiation amount of 1.2 million lux.hr.

9. The solid dosage form according to claim 1, wherein a color difference of the solid dosage form is 420 or less when irradiated with light in a total irradiation amount of 1.2 million lux.hr.

10. A solid dosage form comprising a compound represented by formula (I):

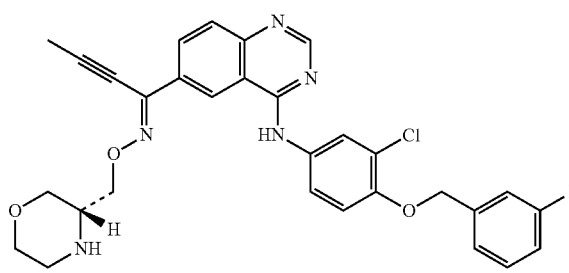

or its pharmaceutically acceptable salt, wherein an increased amount of substances related to the compound represented by formula (I), including the E-form of the compound represented by formula (I), is 0.3% or less from the beginning of an experiment, when irradiated with light in a total irradiation amount of 1.2 million lux.hr.

11. A solid dosage form comprising a compound represented by formula (I):

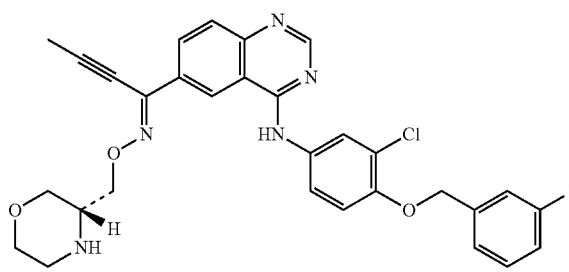

or its pharmaceutically acceptable salt as an active ingredient, wherein a color difference of the formulation is 420 or less when irradiated with light in a total irradiation amount of 1.2 million lux.hr.

12. The solid dosage form according to claim 1, wherein the active ingredient is a hydrochloride or p-toluenesulfonate salt of the compound represented by formula (I).

13. The solid dosage form according to claim 12, wherein the active ingredient is a monohydrochloride salt of the compound represented by formula (I).

14. A method for analyzing a degradation product of a compound represented by formula (I):

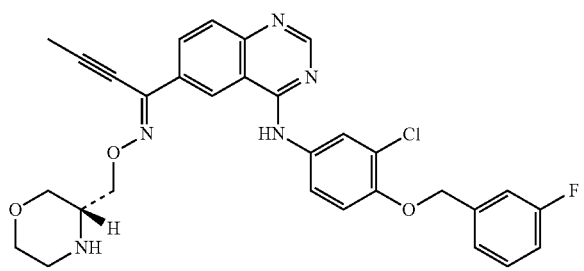

or its pharmaceutically acceptable salt as an active ingredient in a solid dosage form, comprising measuring an amount of substances related to the compound represented by formula (I), including the E-form of the compound represented by formula (I), by high-performance liquid chromatography.

15. A compound represented by the following formula:

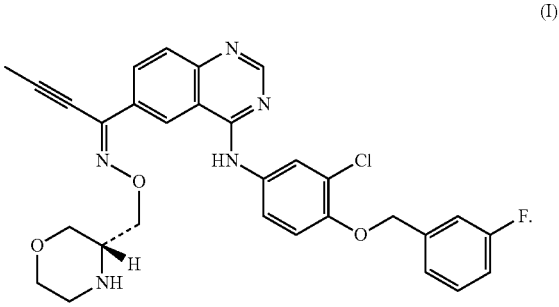

16. A method for reducing a color difference ΔE of a formulation comprising a compound represented by formula (I):

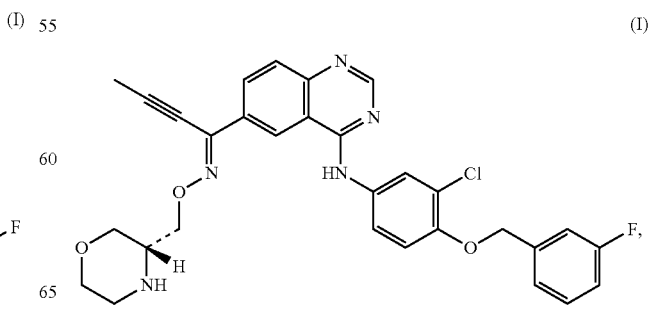

the method comprising reducing an amount of the E-form of the compound represented by formula (I) in the formulation.

* * * * *